US012036264B2

(12) United States Patent
Cadete Pires et al.

(10) Patent No.: US 12,036,264 B2
(45) Date of Patent: Jul. 16, 2024

(54) PHARMACEUTICAL COMPOSITIONS COMPRISING TEIXOBACTIN

(71) Applicant: NovoBiotic Pharmaceuticals, LLC, Cambridge, MA (US)

(72) Inventors: Ana Cristina Cadete Pires, Cambridge, MA (US); Aranda Rae Duan, Medford, MA (US); Losee Lucy Ling, Arlington, MA (US)

(73) Assignee: NovoBiotic Pharmaceuticals, LLC, Cambridge, MA (US)

( * ) Notice: Subject to any disclaimer, the term of this patent is extended or adjusted under 35 U.S.C. 154(b) by 186 days.

(21) Appl. No.: 16/969,598

(22) PCT Filed: Feb. 6, 2019

(86) PCT No.: PCT/US2019/016796

§ 371 (c)(1),
(2) Date: Aug. 13, 2020

(87) PCT Pub. No.: WO2019/160719

PCT Pub. Date: Aug. 22, 2019

(65) Prior Publication Data

US 2021/0052693 A1 Feb. 25, 2021

Related U.S. Application Data

(60) Provisional application No. 62/687,950, filed on Jun. 21, 2018, provisional application No. 62/631,100, filed on Feb. 15, 2018.

(51) Int. Cl.

| | |
|---|---|
| ***A61K 38/15*** | (2006.01) |
| ***A61K 47/24*** | (2006.01) |
| ***A61K 47/26*** | (2006.01) |
| ***A61K 47/34*** | (2017.01) |
| ***A61P 31/06*** | (2006.01) |

(52) U.S. Cl.

CPC .............. *A61K 38/15* (2013.01); *A61K 47/24* (2013.01); *A61K 47/26* (2013.01); *A61K 47/34* (2013.01); *A61P 31/06* (2018.01)

(58) Field of Classification Search

CPC ........ A61K 38/15; A61K 47/24; A61K 47/26; A61K 47/34; A61K 31/4168; A61K 31/685; A61P 31/06; A61P 31/04

See application file for complete search history.

(56) References Cited

U.S. PATENT DOCUMENTS

| | | | |
|---|---|---|---|
| 9,163,065 | B2 | 10/2015 | Peoples et al. |
| 2004/0116360 | A1 | 6/2004 | Kwon |

FOREIGN PATENT DOCUMENTS

| | | | |
|---|---|---|---|
| WO | 2011/160110 | A1 | 12/2011 |

OTHER PUBLICATIONS

Hong Jiang, Self-enhanced targeted delivery of a cell wall- and membrane-active antibiotics, daptomycin, against staphylococcal pneumonia, Acta Pharmaceutica Sinica B 2016;6(4):319-328.*
Biochempeg, mPEG-DSPE(ammonium salt), published online Nov. 2014.*
Ling et al., A new antibiotic kills pathogens without detectable resistance. Nature. Jan. 2015;517(7535):455-9.
Parmar et al., Design and syntheses of highly potent teixobactin analogues against *Staphylococcus aureus*, Methicillin-Resistant *Staphylococcus aureus* (MRSA), and Vancomycin-Resistant Enterococci (VRE) in Vitro and in Vivo. J Med Chem. Mar. 2018;61(5):2009-17.
Tran Le et al., Improved heat stability by whey protein—surfactant interaction. Food Hydrocolloids. 2011;25(4):594-603.
International Search Report and Written Opinion for Application No. PCT/US2019/016796, dated Apr. 24, 2019, 11 pages.
Rawal et al., Combating Tuberculosis Infection: A Forbidding Challenge. Indian J Pharm Sci. Jan.-Feb. 2016;78(1):8-16.

* cited by examiner

*Primary Examiner* — Julie Ha
*Assistant Examiner* — Erinne R Dabkowski
(74) *Attorney, Agent, or Firm* — McCarter & English, LLP; Maria Laccotripe Zacharakis; Yelena Margolin

(57) ABSTRACT

The present invention provides pharmaceutical compositions of teixobactin that are capable of preventing gelation of teixobactin. The pharmaceutical compositions comprise teixobactin and a pegylated phospholipid. The present invention also provides methods of preparing the pharmaceutical compositions of teixobactin and methods of treating a subject using the pharmaceutical compositions of teixobactin.

14 Claims, 7 Drawing Sheets

| No. | Chemical Name | Abbreviated Name | Chemical Structure |
|---|---|---|---|
| 1 | 1,2-dioleoyl-sn-glycero-3-phosphoethanolamine-N-[methoxy(polyethylene glycol)-5000] (ammonium salt) | 18:1 PEG5000 PE | 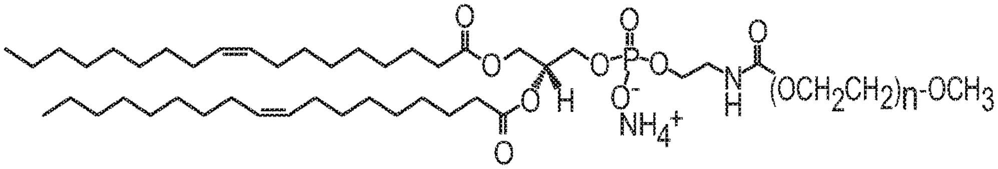 |
| 2 | 1,2-dipalmitoyl-sn-glycero-3-phosphoethanolamine-N-[methoxy(polyethylene glycol)-2000] (ammonium salt) | 16:0 PEG2000 PE | 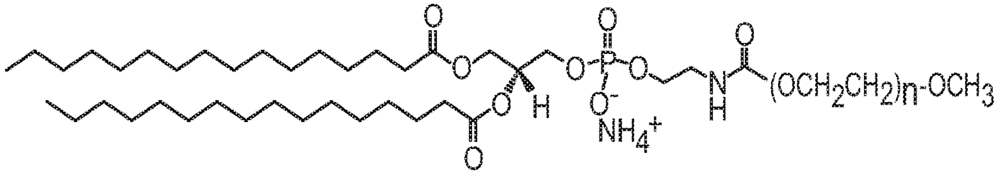 |
| 3 | 1,2-dimyristoyl-sn-glycero-3-phosphoethanolamine-N-[methoxy(polyethylene glycol)-2000] (ammonium salt) | 14:0 PEG2000 PE | 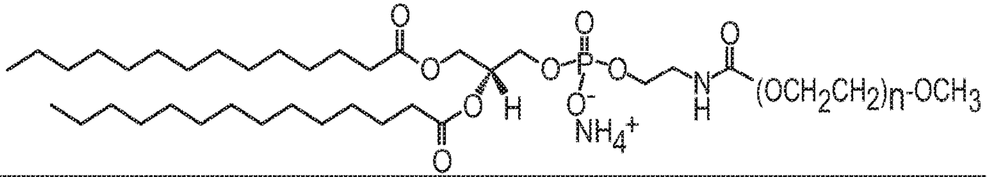 |
| 4 | 1,2-dioleoyl-sn-glycero-3-phosphoethanolamine-N-[methoxy(polyethylene glycol)-2000] (ammonium salt) | 18:1 PEG2000 PE | 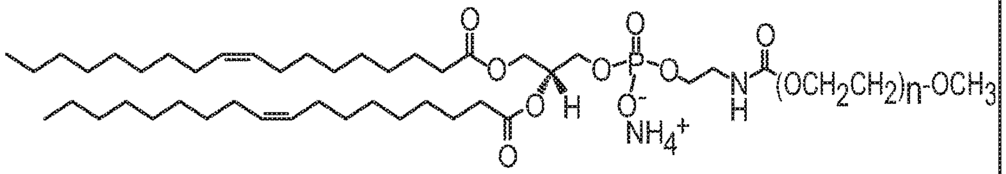 |
| 5 | 1,2-distearoyl-sn-glycero-3-phosphoethanolamine-N-[methoxy(polyethylene glycol)-2000] (ammonium salt) | 18:0 PEG2000 PE | 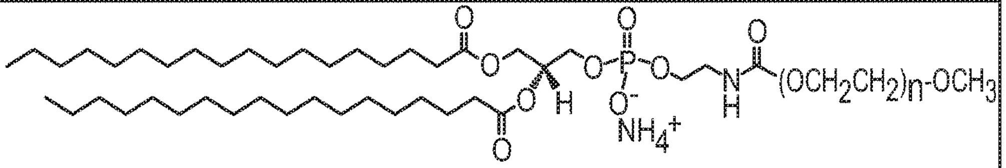 |

FIG. 2

PHARMACEUTICAL COMPOSITIONS COMPRISING TEIXOBACTIN

RELATED APPLICATIONS

This application is a 35 U.S.C. § 371 national stage filing of International Application No. PCT/US2019/016796, filed on Feb. 6, 2019, which claims the benefit of priority to U.S. Provisional Application No. 62/631,100, filed on Feb. 15, 2018 and U.S. Provisional Application No. 62/687,950, filed on Jun. 21, 2018. The entire contents of each of the foregoing applications are incorporated herein by reference.

GOVERNMENT SUPPORT

This invention was made with Government support under SBIR Grant No. R44AI118000-01 awarded by the National Institutes of Health. The Government has certain rights in the invention.

BACKGROUND OF THE INVENTION

Among modern medicine's great achievements is the development and successful use of antimicrobials against disease-causing microbes. Antimicrobials have saved numerous lives and reduced the complications of many diseases and infections. However, the currently available antimicrobials are not as effective as they once were.

Over time, many microbes have developed ways to circumvent the anti-microbial actions of the known antimicrobials, and in recent years there has been a worldwide increase in infections caused by microbes resistant to multiple antimicrobial agents. With the increased availability and ease of global travel, rapid spread of drug-resistant microbes around the world is becoming a serious problem. In the community, microbial resistance can result from nosocomial acquisition of drug-resistant pathogens (e.g., methicillin resistant *Staphylococcus aureus* (MRSA) and vancomycin resistant Enterococci (VRE)); emergence of resistance due to the use of antibiotics within the community (e.g., penicillin- and quinolone-resistant *Neisseria gonorrheae*); acquisition of resistant pathogens as a result of travel (e.g., antibiotic-resistant *Shigella*); or as a result of using antimicrobial agents in animals with subsequent transmission of resistant pathogens to humans (e.g., antibiotic resistant *Salmonella*). Antibiotic resistance in hospitals has usually resulted from overuse of antibiotics and has been a serious problem with MRSA, VRE, and multi-drug resistant Gram-negative bacilli (MDR-GNB) (e.g., *Enterobacter, Klebsiella, Serratia, Citrobacter, Pseudomonas*, and *E. coli*). In particular, catheter-related blood stream infections by bacteria and skin and soft tissue infections (SSTIs) are becoming an increasing problem.

Bacteria, viruses, fungi, and parasites have all developed resistance to known antimicrobials. Resistance usually results from three mechanisms: (i) alteration of the drug target such that the antimicrobial agent binds poorly and thereby has a diminished effect in controlling infection; (ii) reduced access of the drug to its target as a result of impaired drug penetration or active efflux of the drug; and (iii) enzymatic inactivation of the drug by enzymes produced by the microbe. Antimicrobial resistance provides a survival advantage to microbes and makes it harder to eliminate microbial infections from the body. This increased difficulty in fighting microbial infections has led to an increased risk of developing infections in hospitals and other settings. Diseases such as tuberculosis, malaria, gonorrhea, and childhood ear infections are now more difficult to treat than they were just a few decades ago. Drug resistance is a significant problem for hospitals harboring critically ill patients who are less able to fight off infections without the help of antibiotics. Unfortunately, heavy use of antibiotics in these patients selects for changes in microbes that bring about drug resistance. These drug resistant bacteria are resistant to our strongest antibiotics and continue to prey on vulnerable hospital patients. It has been reported that 5 to 10 percent of patients admitted to hospitals acquire an infection during their stay and that this risk has risen steadily in recent decades.

In view of these problems, there is an increasing need for novel antimicrobials to combat microbial infections and the problem of increasing drug resistance. A renewed focus on antimicrobial drug discovery is critical as pathogens are developing resistance to available drugs.

Synthetic compounds have thus far failed to replace natural antibiotics and to lead to novel classes of broad-spectrum compounds, despite the combined efforts of combinatorial synthesis, high-throughput screening, advanced medicinal chemistry, genomics and proteomics, and rational drug design. The problem with obtaining new synthetic antibiotics may be related in part to the fact that the synthetic antibiotics are invariably pumped out across the outer membrane barrier of bacteria by Multidrug Resistance pumps (MDRs). The outer membrane of bacteria is a barrier for amphipathic compounds (which essentially all drugs are), and MDRs extrude drugs across this barrier. Evolution has produced antibiotics that can largely bypass this dual barrier/extrusion mechanism, but synthetic compounds almost invariably fail.

Teixobactin (TXB), described, e.g., in U.S. Pat. Nos. 9,163,065 and 9,402,878, is a newly discovered inhibitor of a broad spectrum of Gram-positive pathogens, MRSA, VRE, vancomycin-intermediate *S. aureus* (VISA), linezolid-resistant *S. aureus*, daptomycin-non-susceptible *S. aureus*, penicillin-resistant *S. pneumoniae* and *M. tuberculosis*. TXB is a highly bactericidal compound that inhibits both peptidoglycan synthesis and wall teichoic acid synthesis by binding non-mutable sites on lipid II and lipid II, which are precursors of cell wall components. TXB's excellent activity against *M. tuberculosis*, the causative agent of tuberculosis (TB), is likely due to binding undecaprenyl-coupled lipid intermediates of peptidoglycan and arabinogalactan in this pathogen. Binding multiple cell wall targets at non-mutable sites suggests that resistance to TXB will be difficult to develop.

TXB has shown many favorable drug properties, such as efficacy in lung, thigh and blood infection models in mice. However, at elevated concentrations, TXB may gelate when exposed to serum. Accordingly, novel pharmaceutical compositions of TXB and TXB analogs, e.g., pharmaceutical compositions in which gelation of TXB at elevated concentrations is prevented or significantly reduced are needed.

SUMMARY OF THE INVENTION

Accordingly, the present invention provides pharmaceutical compositions of TXB and TXB analogs in which gelation of TXB is prevented or significantly reduced. These pharmaceutical compositions of TXB were unexpectedly discovered after the present inventors screened over 1,000 structurally diverse vehicles and vehicle combinations for their ability to prevent or reduce gelation of TXB when present in a pharmaceutical composition of TXB. The results of the screening, described in Example 1, indicate that the ability of a vehicle or a vehicle combination to prevent or reduce gelation of TXB cannot be predicted, even for a vehicle or a vehicle combination that is known for its ability to solubilize hydrophobic molecules, such as TXB. After extensive experimentation, the present inventors discovered that gelation of TXB can be prevented or reduced if a pegylated phospholipid (PPL) is present in a pharmaceutical composition of TXB.

Accordingly, in some embodiments, the present invention provides a pharmaceutical composition comprising TXB, or an analog thereof, and a PPL.

In some aspects, the PPL comprises a phosphoethanolamine moiety covalently attached to at least one lipid chain. In some embodiments, the PPL is a compound of Formula (I):

(I)

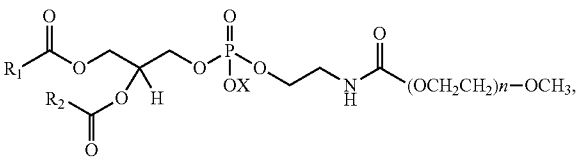

wherein

- $R_1$ and $R_2$ are independently an alkyl chain comprising from 4 to 50 carbon atoms, from 0 to 10 double bonds or from 0 to 10 triple bonds;
- wherein the alkyl chain is unsubstituted or substituted with one or more substituents selected from the group consisting of halogen, —$NO_2$, —COH, —OR', —COR', —OCOR', —COOR', —CONR' and —$SO_4$, wherein R' is hydrogen or a C1-C6 alkyl;
- n is an integer from 5 to 1000; and
- X is a hydrogen, a monovalent cation or a divalent cation.

In some aspects, $R_1$ and $R_2$ are different. In other aspects, $R_1$ and $R_2$ are the same.

In some embodiments, $R_1$ and/or $R_2$ each comprises from 10 to 20 carbon atoms. In some embodiments, $R_1$ and/or $R_2$ each comprises no double or triple bonds. In other embodiments, $R_1$ or $R_2$ comprises at least one double bond. In yet other embodiments, $R_1$ and $R_2$ each comprises at least one double bond.

In some aspects, n is an integer from 30 to 150. In some embodiments, X is selected from the group consisting of hydrogen, $Na^+$, $K^+$, $NH_4^+$, $Ca^{2+}$ and $Mg^{2+}$. In some aspects, X is $NH_4^+$.

In some embodiments, n is an integer from 5 to 500, from 5 to 50, from 10 to 200, from 40 to 120, from 5 to 150, or from 50 to 120. In one embodiment, n is 45. In another embodiment, n is 112. In another embodiment, n is 67. In yet another embodiment, n is 23. In yet another embodiment, n is 17. In yet another embodiment, n is 8.

In some embodiments, the PPL is a compound selected from the group consisting of 1,2-dipalmitoyl-sn-glycero-3-phosphoethanolamine-N-[methoxy(polyethylene glycol)], 1,2-dimyristoyl-sn-glycero-3-phosphoethanolamine-N-[methoxy(polyethylene glycol)], 1,2-dioleoyl-sn-glycero-3-phosphoethanolamine-N-[methoxy(polyethylene glycol)] and 1,2-distearoyl-sn-glycero-3-phosphoethanolamine-N-[methoxy(polyethylene glycol)] of the following structures:

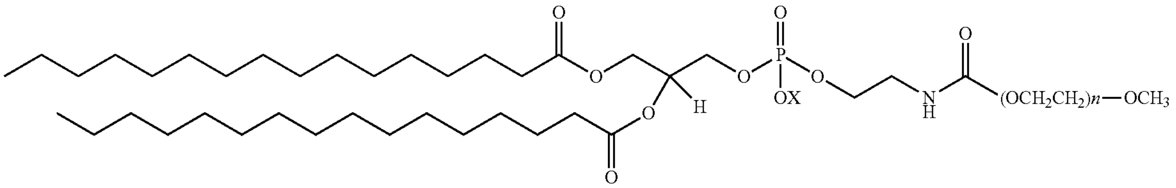

1,2-dipalmitoyl-sn-glycero-3-phosphoethanolamine-N-[methoxy(polyethylene glycol)],

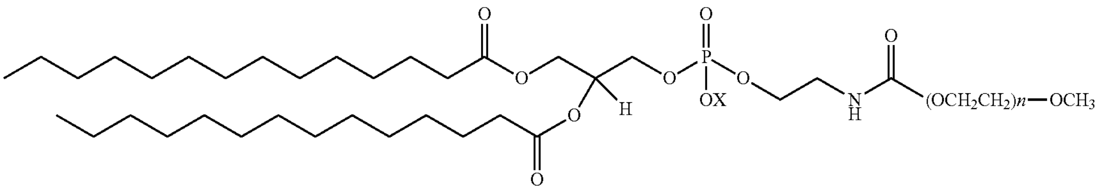

1,2-dimyristoyl-sn-glycero-3-phosphoethanolamine-N-[methoxy(polyethylene glycol)],

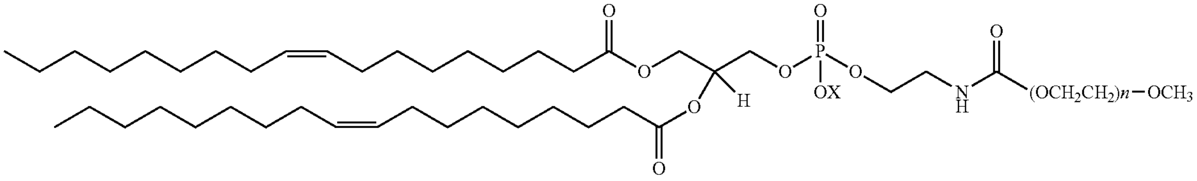

1,2-dioleoyl-sn-glycero-3-phosphoethanolamine-N-[methoxy(polyethylene glycol)]

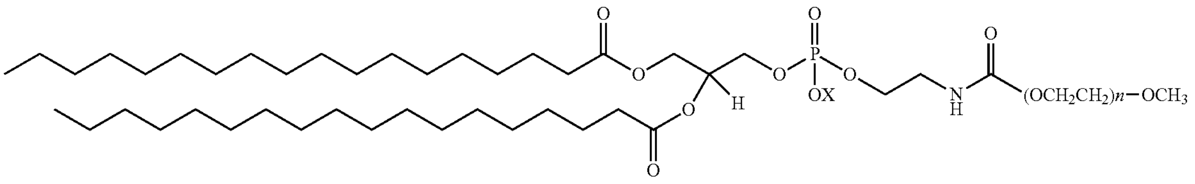

1,2-distearoyl-sn-glycero-3-phosphoethanolamine-N-[methoxy(polyethylene glycol)].

In one embodiment, the PPL is 1,2-dipalmitoyl-sn-glycero-3-phosphoethanolamine-N-[methoxy(polyethylene glycol)], e.g., 1,2-dipalmitoyl-sn-glycero-3-phosphoethanolamine-N-[methoxy(polyethylene glycol)-2000] also referred to as 16:0 PEG2000 PE, shown under No. 2 in FIG. 2.

In one embodiment, the PPL is 1,2-dimyristoyl-sn-glycero-3-phosphoethanolamine-N-[methoxy(polyethylene glycol)], e.g., 1,2-dimyristoyl-sn-glycero-3-phosphoethanolamine-N-[methoxy(polyethylene glycol)-2000] also referred to as 14:0 PEG2000 PE, as shown under No. 3 in FIG. 2.

In one embodiment, the PPL is 1,2-dioleoyl-sn-glycero-3-phosphoethanolamine-N-[methoxy(polyethylene glycol)], e.g., 1,2-dioleoyl-sn-glycero-3-phosphoethanolamine-N-[methoxy(polyethylene glycol)-2000] also referred to as 18:1 PEG2000 PE, as shown under No. 4 in FIG. 2.

In one embodiment, the PPL is 1,2-dioleoyl-sn-glycero-3-phosphoethanolamine-N-[methoxy(polyethylene glycol)], e.g., 1,2-dioleoyl-sn-glycero-3-phosphoethanolamine-N-[methoxy(polyethylene glycol)-5000] also referred to as 18:1 PEG5000 PE, as shown under No. 1 in FIG. 2.

In one embodiment, the PPL is 1,2-distearoyl-sn-glycero-3-phosphoethanolamine-N-[methoxy(polyethylene glycol)], e.g., 1,2-distearoyl-sn-glycero-3-phosphoethanolamine-N-[methoxy(polyethylene glycol)-2000] also referred to as 18:0 PEG2000 PE, as shown under No. 5 in FIG. 2.

In some embodiments, the pharmaceutical composition further comprises a carbohydrate, e.g., a carbohydrate is selected from the group consisting of dextrose, glucose, fructose, galactose, lactose, sucrose, ribose, xylose, threose, mannose and mannitol.

In some embodiments, the weight ratio of PPL to teixobactin in the pharmaceutical composition is about 1:1 (w/w) PPL:TXB or greater. For example, in some embodiments, the weight ratio of PPL to teixobactin is between about 1:1 (w/w) and about 10:1 (w/w) PPL:TXB, e.g., about 1:1 (w/w), about 1.5:1 (w/w), about 2:1 (w/w), about 2.5:1 (w/w), about 3:1 (w/w), about 3.5:1 (w/w), about 4:1 (w/w), about 4.5:1 (w/w), about 5:1 (w/w), about 5.5:1 (w/w), about 6:1 (w/w), about 6.5:1 (w/w), about 7:1 (w/w), about 7.5:1 (w/w), about 8:1 (w/w), about 8.5:1 (w/w), about 9:1 (w/w), about 9.5:1 (w/w) or about 10:1 (w/w) PPL:TXB.

In some aspects, the molar ratio of PPL to teixobactin of about 0.1:1 or greater PPL:TXB. For example, in some embodiments, the molar ratio of PPL to TXB in the pharmaceutical compositions is between about 0.1:1 and about 10:1 PPL:TXB, e.g., about 0.1:1, about 0.2:1, about 0.3:1, about 0.4:1, about 0.5:1, about 0.6:1, about 0.7:1, about 0.8:1, about 0.9:1, about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1 or about 10:1 PPL:TXB.

In some embodiments, the present invention also provides a method of preparing a pharmaceutical composition of TXB that comprises the following steps:

providing an aqueous solution comprising PPL; and adding teixobactin to the aqueous solution comprising PPL.

In some embodiments, the method comprises the following steps:

providing an aqueous solution comprising PPL;

adding teixobactin to the aqueous solution comprising PPL; and adding a carbohydrate to the aqueous solution comprising PPL and teixobactin.

In some aspects, the present invention also provides a method for treating a bacterial infection in a subject in need thereof that comprises administering to said subject a pharmaceutical composition of the present invention comprising TXB. In one embodiment, the pharmaceutical composition is administered intravenously.

In further embodiments, the bacterial infection is caused by methicillin resistant *Staphylococcus aureus* (MRSA) or by a *Mycobacterium tuberculosis*.

In some embodiments, the subject is a human.

BRIEF DESCRIPTION OF THE DRAWINGS

FIG. 2 shows names and structures of exemplary PPLs in the form of ammonium salts.

DETAILED DESCRIPTION OF THE INVENTION

Figure 1:
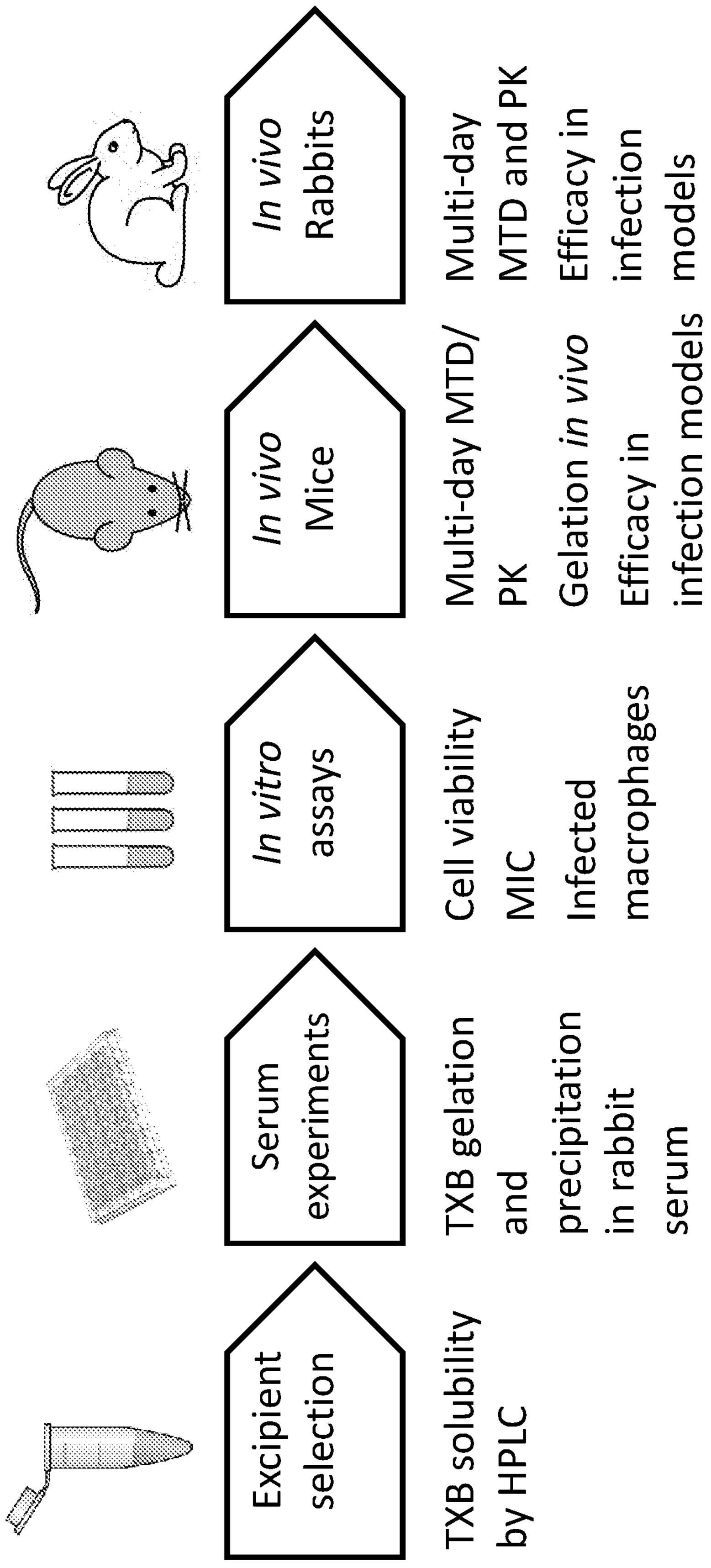
FIG. 1 is a schematic illustration of the procedure used to screen the vehicles for preparing a pharmaceutical composition of teixobactin.

The present invention is based on a surprising discovery that gelation of TXB, e.g., gelation of TXB in serum, can be prevented or significantly reduced if TXB is administered to a subject as a part of a pharmaceutical composition that also comprises a pegylated phospholipid (PPL).

Pharmaceutical Compositions of the Invention

In some embodiments, the present invention provides a pharmaceutical composition comprising teixobactin (TXB) or a teixobactin analog (TXB analog) and a pegylated phospholipid (PPL). As used herein, the term "teixobactin", used interchangeably with the term "TXB", encompasses a depsipeptide of the following structural formula:

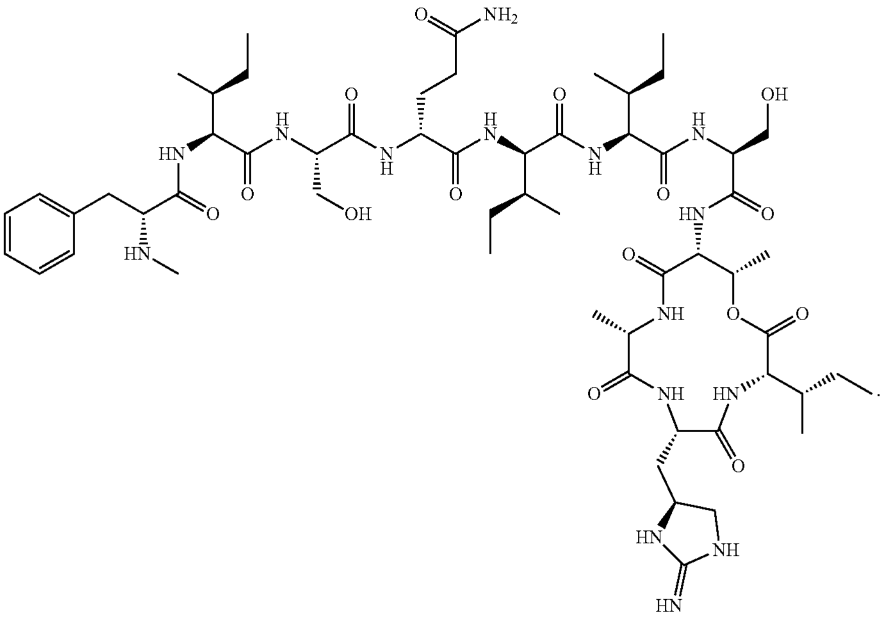 [SMILES: CC[C@H](C)[C@H](NC(=O)[C@@H](Cc1ccccc1)NC)C(=O)N[C@@H](CO)C(=O)N[C@H](CCC(N)=O)C(=O)N[C@@H](C(=O)N[C@H](C(=O)N[C@@H](CO)C(=O)N[C@H]1C(=O)N[C@@H](C)C(=O)N[C@@H](C[C@H]2CNC(=N)N2)C(=O)N[C@@H]([C@@H](C)CC)C(=O)O[C@H]1C)[C@@H](C)CC)[C@@H](C)CC]

TXB is described, e.g., in U.S. Pat. Nos. 9,163,065 and 9,402,878, the entire contents of each of which are incorporated herein by reference. The term "teixobactin" also comprises tautomers of teixobactin or salts of teixobactin, e.g., pharmaceutically acceptable salts of teixobactin.

As used herein, the term "teixobactin analog", used interchangeably with the term "TXB analog", encompasses any compound having a chemical structure similar to that of TXB and exhibiting antibacterial activity. In some embodiments, a TXB analog is obtained by modifying the chemical structure of TXB. Non-limiting examples of TXB analogs encompassed by the present invention comprise TXB analogs described in, e.g., Yang et al., *Chem Commun* (*Camb*). 2017 Feb. 28; 53(18):2772-2775; Jin et al., *Bioorg Med Chem.* 2017 Sep. 15; 25(18):4990-4995; Parmar et al., *Chem Commun* (*Camb*). 2017 Jul. 6; 53(55):7788-7791; Fiers et al., *ACS Infect Dis.* 2017 Oct. 13; 3(10):688-690; Abdel Monaim et al., *J Med Chem.* 2017 Sep. 14; 60(17):7476-7482; Monaim et al., *Molecules.* 2017 Sep. 28; 22(10); Chen et al., *Chem Commun* (*Camb*). 2017 Oct. 12; 53(82):11357-11359; Guo et al., *Chemistry.* 2017 Oct. 9. doi: 10.1002/chem.201704167; Schumacher et al., *Org Biomol Chem.* 2017 Oct. 25; 15(41):8755-8760; Abdel Monaim et al., *Bioorg Med Chem.* 2017 Sep. 30. pii: S0968-0896(17) 31609-7; Singh, *Future Med Chem.* 2018 January; 10(2): 133-134; Mandalapu et al., *J Org Chem.* 2018 Jan. 31. doi: 10.1021/acs.joc.7b02462; Parmar et al., *J Med Chem.* 2018 Jan. 24. doi: 10.1021/acs.jmedchem.7b01634; Jin et al., *Bioorg Med Chem.* 2018 Feb. 1. pii: S0968-0896(18)30002-6; Parmar et al., *Chem Commun* (*Camb*). 2016 Apr. 26; 52(36):6060-3; Parmar et al., *Chem Commun* (*Camb*). 2017 Feb. 7; 53(12):2016-2019; and Yad et al., *Org Lett.* 2015 Dec. 18; 17(24):6182-5, the entire contents of each of which are hereby incorporated herein by reference.

The term "salt" or "salts", as used herein, encompasses acidic salts formed with inorganic and/or organic acids. In one embodiment, a salt may be a pharmaceutically acceptable salt, e.g., a non-toxic salt. Salts of TXB may be formed, for example, by reacting TXB with an amount of acid, such as an equivalent amount, in a medium such as one in which the salt precipitates or in an aqueous or aqueous and organic medium followed by lyophilization.

TXB also contains a basic moiety, e.g., an amine or a guanidine, and, thus, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like. In some embodiments, TXB may be in the form of a chloride salt, e.g., a dichloride salt.

In some embodiments, TXB is a natural product isolated from a bacterial species, e.g., a natural product of a bacterial isolate ISO18629. The bacterial isolate ISO18629 was deposited with Agricultural Research Service Culture Collection (NRRL), National Center for Agricultural Utilization Research, Agricultural Research Service, U.S. Department of Agriculture, 1815 North University Street, Peoria, Illinois 61604, on Sep. 6, 2013, and assigned NRRL Accession Number B-50868 In a specific embodiment, teixobactin may be isolated from an in vitro culture of the bacterial isolate ISO18629.

A pharmaceutical composition of the invention comprises at least one pegylated phospholipid (PPL). The term "pegylated phospholipid", used interchangeably with the term "PPL", refers to a molecule that comprises a phospholipid and polyethylene glycol (PEG). In some embodiments, the phospholipid may be covalently attached to PEG. In some embodiments, the phospholipid may comprise a lipid tail that further comprises at least one double bond or at least one triple bond.

The PPL may be present in the pharmaceutical compositions of the present invention in the form of a salt, e.g., a pharmaceutically acceptable salt, such as a sodium salt, a potassium salt, an ammonium salt, a calcium salt or an ammonium salt. In one specific embodiment, the PPL is present in the pharmaceutical compositions of the invention in the form of an ammonium salt. In another specific embodiment, the PPL is present in the pharmaceutical compositions of the invention as a sodium salt.

The phospholipid that is a part of PPL may be any phospholipid known in the art. Non-limiting examples of phospholipids useful in the context of the present invention include glycerophospholipids, e.g., phosphatidic acid (phosphatidate, PA), phosphatidylethanolamine (cephalin, PE), phosphatidylcholine (lecithin, PC), phosphatidylserine (PS) and phosphoinositides, such as phosphatidylinositol (PI), phosphatidylinositol phosphate (PIP), phosphatidylinositol bisphosphate (PIP2) and phosphatidylinositol trisphosphate (PIP3). Non-limiting examples of phospholipids also include phosphosphingolipids, e.g., ceramide phosphorylcholine (sphingomyelin, SPH), ceramide phosphorylethanolamine (sphingomyelin, Cer-PE) and ceramide phosphoryllipid.

Non-limiting of phospholipids that may be a part of PPL also include phospholipids comprising a phosphoethanolamine moiety that is covalently attached to at least one lipid chain, e.g., an alkyl chain comprising from 4 to 50 carbon atoms, from 0 to 10 double bonds or from 0 to 10 triple bonds.

The term "polyethylene glycol", used interchangeably with the term "PEG", refers to an oligomer or polymer of ethylene oxide. In some embodiments, PEG is covalently attached to a phospholipid, resulting in a pegylated phospholipid (PPL). In some aspects, PEG comprises at least 5 ethylene oxide units, e.g., at least 10 units, at least 20 units, at least 40 units, at least 50 units, at least 100 units, at least 200 units, at least 300 units, at least 500 units, at least 600 units, at least 700 units, at least 800 units, at least 900 units or at least 1000 units. In some embodiments, the PEG has an average molecular weight (average MW) of at least about 50 Daltons (Da), at least about 100 Da, at least about 200 Da, at least about 300 Da, at least about 400 Da, at least about 500 Da, at least about 600 Da, at least about 700 Da, at least about 800 Da, at least about 900 Da, at least about 1000 Da, at least about 1500 Da, at least about 2000 Da, at least about 2500 Da, at least about 3000 Da, at least about 3500 Da, at least about 4000 Da, at least about 4500 Da, at least about 5000 Da, at least about 5500 Da, at least about 6000 Da, at least about 6500 Da, at least about 7000 Da, at least about 7500 Da, at least about 8000 Da, at least about 8500 Da, at least about 9000 Da, at least about 9500 Da or at least about 10000 Da. In one specific embodiment, the average MW of PEG useful in the context of the present invention is 2000 Da. In another specific embodiment, the average MW of PEG is 5000 Da.

In some examples, the PPL comprises a phospholipid comprising a phosphoethanolamine moiety and PEG and is a compound of Formula (I):

(I)

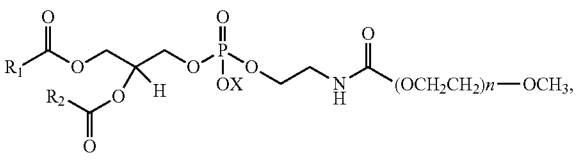

wherein $R_1$ and $R_2$ are independently an alkyl chain comprising from 4 to 50 carbon atoms, from 0 to 10 double bonds or from 0 to 10 triple bonds;

wherein the alkyl chain is unsubstituted or substituted with one or more substituents selected from the group consisting of halogen, —$NO_2$, —COH, —OR', —COR', —OCOR', —COOR', —CONR' and —$SO_4$, wherein R' is hydrogen or a C1-C6 alkyl;

n is an integer from 5 to 1000; and

X is a hydrogen, a monovalent cation or a divalent cation.

In some examples, $R_1$ and $R_2$ may be different. In other examples, $R_1$ and $R_2$ may be the same.

In some embodiments, $R_1$ and $R_2$ may comprise from 10 to 20 carbon atoms. In certain embodiments, $R_1$ and $R_2$ may comprise no double or triple bonds, or may each comprise at least one double bond.

In Formula (I), n denotes the number of ethylene glycol units, and may be an integer from 30 to 150, e.g., from 30 to 50, from 40 to 100, from 60 to 80, from 70 to 120 or from 100 to 150.

In Formula (I), X may be selected from the group consisting of hydrogen, $Na^+$, $K^+$, $NH_4^+$, $Ca_2^+$ and $Mg_2^+$. In one specific embodiment, X is $NH_4^+$. In another specific embodiment, X is $Na^+$.

In some examples, the PPL of Formula (I) may be a compound selected from the group consisting of 1,2-dipalmitoyl-sn-glycero-3-phosphoethanolamine-N-[methoxy (polyethylene glycol)], 1,2-dimyristoyl-sn-glycero-3-phosphoethanolamine-N-[methoxy(polyethylene glycol)], 1,2-dioleoyl-sn-glycero-3-phosphoethanolamine-N-[methoxy (polyethylene glycol)] and 1,2-distearoyl-sn-glycero-3-phosphoethanolamine-N-[methoxy(polyethylene glycol)] of the following structures:

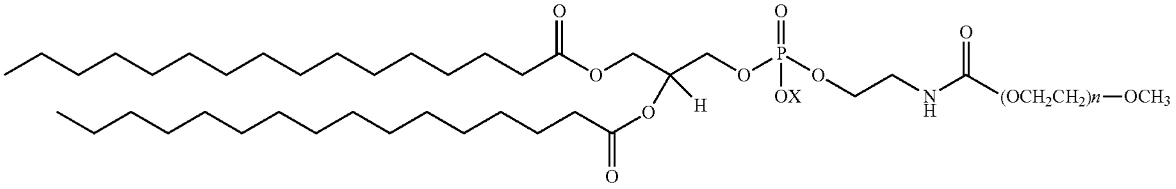

1,2-dipalmitoyl-sn-glycero-3-phosphoethanolamine-N-[methoxy(polyethylene glycol)],

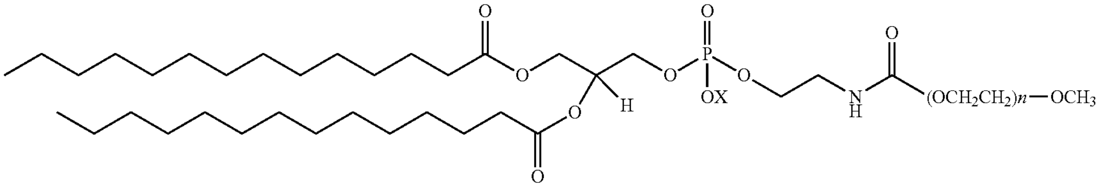

1,2-dimyristoyl-sn-glycero-3-phosphoethanolamine-N-[methoxy(polyethylene glycol)],

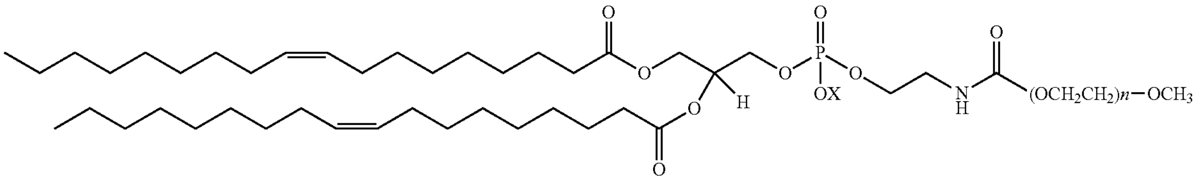

1,2-dioleoyl-sn-glycero-3-phosphoethanolamine-N-[methoxy(polyethylene glycol)]

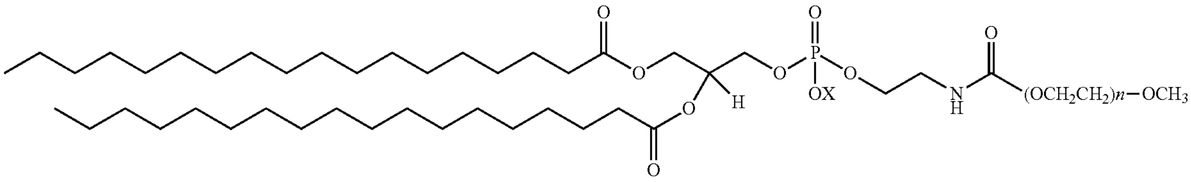

1,2-distearoyl-sn-glycero-3-phosphoethanolamine-N-[methoxy(polyethylene glycol)].

In one specific embodiment, the PPL of Formula (I) is 1,2-distearoyl-sn-glycero-3-phosphoethanolamine-N-[methoxy(polyethylene glycol)] of the following structure:

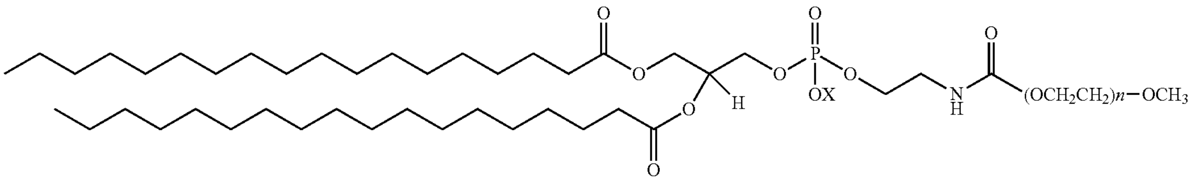

1,2-distearoyl-sn-glycero-3-phosphoethanolamine-N-[methoxy(polyethylene glycol)].

In one example, the PPL may be 1,2-dipalmitoyl-sn-glycero-3-phosphoethanolamine-N-[methoxy(polyethylene glycol)], e.g., 1,2-dipalmitoyl-sn-glycero-3-phosphoethanolamine-N-[methoxy(polyethylene glycol)-2000], also referred to as 16:0 PEG2000 PE, shown under No. 2 in FIG. 2. The 16:0 PEG2000 PE comprises PEG having an average molecular weight of 2000 Da.

In another example, the PPL may be 1,2-dimyristoyl-sn-glycero-3-phosphoethanolamine-N-[methoxy(polyethylene glycol)], e.g., 1,2-dimyristoyl-sn-glycero-3-phosphoethanolamine-N-[methoxy(polyethylene glycol)-2000], also referred to as 14:0 PEG2000 PE, as shown under No. 3 in FIG. 2. The 14:0 PEG2000 PE comprises PEG having an average molecular weight of 2000 Da.

In another example, the PPL may be 1,2-dioleoyl-sn-glycero-3-phosphoethanolamine-N-[methoxy(polyethylene glycol)], e.g., 1,2-dioleoyl-sn-glycero-3-phosphoethanolamine-N-[methoxy(polyethylene glycol)-2000], also referred to as 18:1 PEG2000 PE, as shown under No. 4 in FIG. 2. The 18:1 PEG2000 PE comprises PEG having an average molecular weight of 2000 Da.

In yet another example, the PPL may be 1,2-dioleoyl-sn-glycero-3-phosphoethanolamine-N-[methoxy(polyethylene glycol)], e.g., 1,2-dioleoyl-sn-glycero-3-phosphoethanolamine-N-[methoxy(polyethylene glycol)-5000], also referred to as 18:1 PEG5000 PE, as shown under No. 1 in FIG. 2. The 18:1 PEG5000 PE comprises PEG having an average molecular weight of 5000 Da.

In yet another example, the PPL may be 1,2-distearoyl-sn-glycero-3-phosphoethanolamine-N-[methoxy(polyethylene glycol)], e.g., 1,2-distearoyl-sn-glycero-3-phosphoethanolamine-N-[methoxy(polyethylene glycol)-2000], also referred to as 18:0 PEG2000 PE, as shown under No. 5 in FIG. 2. The 18:0 PEG2000 PE comprises PEG having an average molecular weight of 2000 Da.

The PPL and TXB may be present in the pharmaceutical compositions of the present invention at a weight ratio of PPL to teixobactin of about 1:1 (w/w) or greater PPL:TXB. For example, the weight ratio of PPL to TXB in the pharmaceutical compositions of the invention may be between about 1:1 (w/w) and about 10:1 (w/w) PPL:TXB, e.g., about 1:1 (w/w), about 1.5:1 (w/w), about 2:1 (w/w), about 2.5:1 (w/w), about 3:1 (w/w), about 3.5:1 (w/w), about 4:1 (w/w), about 4.5:1 (w/w), about 5:1 (w/w), about 5.5:1 (w/w), about 6:1 (w/w), about 6.5:1 (w/w), about 7:1 (w/w), about 7.5:1 (w/w), about 8:1 (w/w), about 8.5:1 (w/w), about 9:1 (w/w), about 9.5:1 (w/w) or about 10:1 (w/w) PPL:TXB. In one specific embodiment, the weight ratio of PPL to TXB in the pharmaceutical composition of the invention is about 1:1 (w/w). In certain embodiments of the present invention, the weight ratio of PPL to TXB is not lower than about 1:1 PPL:TXB (w/w). When the PPL is 1,2-distearoyl-sn-glycero-3-phosphoethanolamine-N-[methoxy(polyethylene glycol)], Applicant has surprisingly discovered that gelation of TXB occurs when the weight ratio of PPL to TXB is lower than about 1:1 PPL:TXB (w/w).

In some embodiments, the PPL and TXB may be present in the pharmaceutical compositions of the present invention at molar ratio of PPL to teixobactin of about 0.1:1 or greater. For example, the molar ratio of PPL to TXB in the pharmaceutical compositions of the invention may be between about 0.1:1 and about 10:1 PPL:TXB, e.g., about 0.1:1, about 0.2:1, about 0.3:1, about 0.4:1, about 0.5:1, about 0.6:1, about 0.7:1, about 0.8:1, about 0.9:1, about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1 or about 10:1 PPL:TXB. In one embodiment, the molar ratio of PPL to TXB in the pharmaceutical composition of the invention is about 0.1:1 PPL:TXB. In another embodiment, the molar ratio of PPL to TXB in the pharmaceutical composition of the invention is about 0.5:1 PPL:TXB. In another embodiment, the molar ratio of PPL to TXB in the pharmaceutical composition of the invention is about 1:1 PPL:TXB. In yet another embodiment, the molar ratio of PPL to TXB in the pharmaceutical composition of the invention is about 2:1 PPL:TXB. In yet embodiment, the molar ratio of PPL to TXB in the pharmaceutical composition of the invention is about 5:1 PPL:TXB. In certain embodiments of the present invention, the molar ratio of PPL to TXB is not lower than about 1:1 PPL:TXB.

The pharmaceutical composition of the present invention may further comprise additional ingredients. In one embodiment, the additional ingredient is a carbohydrate. Non-limiting examples of a carbohydrate suitable for use in the pharmaceutical compositions of the present invention include dextrose, glucose, fructose, galactose, lactose, sucrose, ribose, xylose, threose, mannose and mannitol. In one specific example, the carbohydrate is xylose. In another specific example, the carbohydrate is glucose. In yet another specific example, the carbohydrate is dextrose. In yet another specific example, the carbohydrate is sucrose. In yet another specific example, the carbohydrate is galactose.

The pharmaceutical compositions of the present invention allow administering TXB to a subject, such that a therapeutically effective concentration of TXB is achieved in the subject while gelation of TXB is avoided or significantly reduced. In certain embodiments, the pharmaceutical compositions of the present invention prevent gelation of TXB when TXB is present in the serum of a subject at a concentration of TXB of about 30 μg/mL or greater, e.g., about 40 μg/mL or about 50 μg/mL or greater. In certain embodiments, gelation of TXB when it is present in the pharmaceutical composition of the invention comprising PPL is reduced by at least about 10%, e.g., at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%, as compared to gelation of TXB when it is present in an aqueous solution without PPL.

Methods of Preparing the Pharmaceutical Compositions of the Invention

The pharmaceutical compositions of the invention may be prepared by any method that one of ordinary skill in the art would recognize as suitable for preparing the pharmaceutical compositions. An exemplary method for preparing the pharmaceutical compositions of the invention may comprise the following steps:

providing an aqueous solution comprising PPL; and
adding TXB to the aqueous solution comprising PPL.

In a further example, the method for preparing the pharmaceutical composition of the invention may comprise the following steps:

providing an aqueous solution comprising PPL;
adding TXB to the aqueous solution comprising PPL; and
adding a carbohydrate to the aqueous solution comprising PPL and TXB.

In some embodiments, the carbohydrate may be selected from the group consisting of dextrose, glucose, fructose, galactose, lactose, sucrose, ribose, xylose, threose, mannose and mannitol.

The present inventors have unexpectedly discovered that maintaining the sequence of steps as outlined above, e.g., adding TXB to an aqueous solution comprising PPL or adding TXB to an aqueous solution comprising PPL and subsequently adding a carbohydrate to the aqueous solution, was critical for ensuring that an effective pharmaceutical composition of TXB is formed. If the ingredients of the pharmaceutical composition, i.e., PPL, TXB or PPL, TXB and a carbohydrate are added together in an order that is different from the order specified above, the an effective pharmaceutical composition of TXB may not form.

Methods of Treatment Using the Pharmaceutical Compositions of the Invention

The present invention also provides methods of treating an infection with a pathogen.

The methods comprise administering to a subject in need thereof a pharmaceutical composition of the invention, thereby treating the infection with the pathogen in the subject. In some embodiments, the methods of the invention also comprise inhibiting growth of a pathogen and comprise contacting the pathogen with the pharmaceutical composition of the invention, thereby inhibiting the growth of the pathogen. Non-limiting examples of a pathogen include, but are not limited to, a bacterium, a fungus, a virus, a protozoan, a helminth, a parasite, and combinations thereof.

In some embodiments, a pharmaceutical composition of the invention is administered in an effective amount to a subject in need thereof. The term “effective amount”, as used herein, refers to the amount of the pharmaceutical composition that is effective to produce a desired effect in the subject, e.g., an animal. It is recognized that when an agent is being used to achieve a therapeutic effect, the actual dose which comprises the “effective amount” will vary depending on a number of conditions including, but not limited to, the particular condition being treated, the severity of the disease, the size and health of the patient and the route of administration. A skilled medical practitioner can readily determine the appropriate effective amount using methods well known in the medical arts. In some embodiments, an effective amount is the amount effective to treat a disorder in a subject in need thereof, e.g., to treat an infection with a pathogen. In other embodiments, an effective amount is the amount effective to inhibit growth of a pathogen in a subject, e.g., as compared to growth of the pathogen when the pharmaceutical composition of the invention is not administered to the subject. In yet other embodiments, the effective amount also comprises an amount effective to reduce growth of the pathogen, e.g., as compared to the growth of the pathogen when the pharmaceutical composition of the invention is not administered to the subject. In yet another embodiment, the effective amount is the amount of the pharmaceutical composition of the invention that, when administered to a subject infected with a pathogen, or contacted with a pathogen, results in killing of the pathogen.

Furthermore, a skilled practitioner will appreciate that the effective amount of the pharmaceutical composition of the invention may be lowered or increased by fine-tuning and/or by administering the pharmaceutical composition of the invention alone, or in combination with another therapeutic agent (e.g., an antibiotic agent, an antifungal agent, an antiviral agent, an NSAID, a DMARD, a steroid, etc.). An effective amount may be determined, for example, empirically by starting at a relatively low amount and increasing the amount step-wise with concurrent evaluation of the beneficial effect (e.g., reduction in symptoms). The actual effective amount will be established by dose/response assays using methods standard in the art (Johnson et al., Diabetes. 42:1179, (1993)). As is known to those in the art, the effective amount will depend on bioavailability, bioactivity, and biodegradability of the TXB and the pharmaceutical composition comprising TXB.

In some embodiments, an effective amount of the pharmaceutical composition of the invention is an amount that is sufficient to reduce symptoms of a disorder in a subject, e.g., symptoms of an infection with a pathogen. Accordingly, the effective amount may vary depending on the subject being treated. For example, the effective amount of the pharmaceutical composition of the invention comprises an amount of TXB sufficient to administer a dose of TXB to a subject from about 1 μg/kg body weight to about 100 mg/kg body weight, e.g., about 1 μg/kg to about 100 μg/kg, about 50 mg/kg to about 500 mg/kg, about 200 mg/kg to about 1 mg/kg, about 800 μg/kg to about 10 mg/kg, about 1 mg/kg to about 10 mg/kg, about 5 mg/kg to about 20 mg/kg, about 15 mg/kg to about 40 mg/kg, about 25 mg/kg to about 50 mg/kg, about 30 mg/kg to about 65 mg/kg/about 50 mg/kg to about 75 mg/kg, about 60 mg/kg to about 80 mg/kg, about 75 mg/kg to about 95 kg or about 80 mg/kg to about 100 mg/kg.

In some embodiments, an effective amount of the pharmaceutical composition of the invention comprises a dose of TXB that is between about 1 mg to about 1000 mg, e.g., about 1 mg to about 10 mg, about 5 mg to about 20 mg, about 10 mg to about 50 mg, about 25 mg to about 70 mg, about 40 mg to about 85 mg, about 70 mg to about 100 mg, about 90 mg to about 200 mg, about 100 mg to about 250 mg, about 200 mg to about 500 mg, about 400 mg to about 700 mg, about 500 mg to about 750 mg or about 650 mg to about 1000 mg.

Administration of the pharmaceutical composition of the invention may be hourly, daily, weekly, monthly, yearly, or a single event. In addition, the administration can have a duration of from one day to one year or more. In some embodiments, the administration may refer to daily administration for a period of time, e.g., for about a week, two weeks, three weeks, one month, three months, six months or a year. In some embodiments, the administration may refer to weekly administration for a period of time, e.g., for about a month, three months, six months, one year or more.

As described herein, the pharmaceutical compositions of the invention are useful in methods of treating an infection with a pathogen or in methods of inhibiting growth of a pathogen. In some embodiments, a pathogen may be a bacterium, e.g., a Gram-positive or a Gram negative bacterium. Non-limiting examples of Gram-positive bacteria include *Streptococcus, Staphylococcus, Enterococcus, Corynebacteria, Listeria, Bacillus, Erysipelothrix*, and *Actinomycetes*. In some embodiments, the pharmaceutical compositions of the invention are useful for treating an infection by one or more of: *Helicobacter pylori, Legionella pneumophilia, Mycobacterium tuberculosis, Mycobacterium avium, Mycobacterium intracellulare, Mycobacterium kansaii, Mycobacterium gordonae, Mycobacteria sporozoites, Staphylococcus aureus, Staphylococcus epidermidis, Neisseria gonorrhoeae, Neisseria meningitidis, Listeria monocytogenes, Streptococcus pyogenes* (Group A *Streptococcus*), *Streptococcus agalactiae pyogenes* (Group B *Streptococcus*), *Streptococcus dysgalactia, Streptococcus faecalis, Streptococcus bovis, Streptococcus pneumoniae*, pathogenic *Campylobacter sporozoites, Enterococcus sporozoites, Haemophilus influenzae, Pseudomonas aeruginosa, Bacillus anthracis, Bacillus subtilis, Escherichia coli, Corynebacterium diphtheriae, Corynebacterium jeikeium, Corynebacterium* sporozoites, *Erysipelothrix rhusiopathiae, Clostridium perfringens, Clostridium tetani, Clostridium difficile, Enterobacter aerogenes, Klebsiella pneumoniae,*

*Pasteurella multocida, Bacteroides thetaiotamicron, Bacteroides uniformis, Bacteroides vulgatus, Fusobacterium nucleatum, Streptobacillus moniliformis, Leptospira, and Actinomyces israelli*. In specific embodiments, the pharmaceutical compositions of the invention are useful for treating an infection by Methicillin Resistant *Staphylococcus aureus* (MRSA) or by Vancomycin Resistant Entercocci (VRE). MRSA contributes to approximately 19,000 deaths annually in the United States. Although most of these deaths are due to hospital-acquired MRSA (HA-MRSA), community-acquired MRSA (CA-MRSA) is actually more virulent, and known to be potentially fatal to previously healthy individuals. The virulence of CA-MRSA is in part due to the expression of phenol soluble modulins or PSM peptides. Accordingly, in treating CA-MRSA, one can use the pharmaceutical composition of the invention in combination with an agent that modulates the expression and/or activity of virulence factors, such as, but not limited to, PSM peptides. In certain embodiments, the pharmaceutical compositions of the invention may be useful for treating an infection by spirochetes such as *Borelia burgdorferi, Treponema pallidium*, and *Treponema pertenue*.

In a particular embodiment, the Gram-positive bacteria may be selected from the group consisting of *Staphylococcus* (including, for example, *S. aureus* spp., *S. epidermidis* spp., *S. warneri* spp. and *S. haemolyticus* spp.); *Streptococcus* (including, for example, *S. viridans* spp., *S. pneumoniae* spp., *S. agalactiae* spp., and *S. pyogenes* spp.); *Bacillus* (including, for example, *B. anthracis* spp. and *B. subtilis*, spp.); *Clostridium* (including, for example, *C. difficile* spp.); *Propionibacterium* (including, for example, *P. acnes* spp.); *Enterococcus* (including, for example, *E. faecium* spp., *E. faecalis* spp., Vancomycin-resistant *E. faecium* spp., and Vancomycin-resistant *E. faecalis* spp.,); and *Mycobacterium* (including, for example, *M. smegmatis* spp. and *M. tuberculosis* spp.). In a specific embodiment, the bacteria is *M. tuberculosis*.

The pharmaceutical compositions of the invention described herein are useful for treating disorders caused by these bacteria. Examples of such disorders include acute bacterial skin and skin structure infections, *C. difficile* associated diarrhea, anthrax, sepsis, botulism, urinary tract infections, bacteremia, bacterial endocarditis, diverticulitis, meningitis, pneumonia, and tuberculosis.

The pharmaceutical compositions of the invention are useful for treating disorders caused by these bacteria. Examples of such disorders include influenza, bacteremia, pneumonia, acute bacterial meningitis, gonorrhea, urinary tract infections, respiratory tract infections, catheter-associated bacteremia, wound infections, otitis media, bronchitis, sinusitis, and laryngitis.

In the methods of the present invention, the pharmaceutical composition comprising TXB is administered to a subject in need thereof. The term "subject", as used herein, comprises an animal, e.g., a mammal, including, but not limited to: a pet (e.g., a cat, a dog, a ferret, etc.); a farm animal (e.g., a cow, a sheep, a pig, a horse, a goat, etc.); a laboratory animal (e.g., a rat, a mouse, a monkey, etc.); and a primate (e.g., a chimpanzee, a human or a gorilla). In a specific embodiment, the subject is a human.

Administration of the Pharmaceutical Compositions of the Invention

The pharmaceutical compositions of the invention may be administered by any method known in the art, e.g., locally or systemically. Exemplary routes of administration include oral, parenteral, transdermal, intradermal, intramuscular, intraperitoneal, intravenous, subcutaneous, intranasal (e.g., by a nebulizer, inhaler or an aerosol dispenser), intraocular (e.g., for the treatment of conjunctivitis), intraaural (e.g., for the treatment of ear infections), colorectal, rectal, intravaginal, and any combinations thereof. In addition, it may be desirable to introduce the pharmaceutical compositions of the present invention into the central nervous system by any suitable route, including intraventricular and intrathecal injection. Intraventricular injection may be facilitated by an intraventricular catheter, for example, attached to a reservoir, such as an Ommaya reservoir. Methods of introduction may also be provided by a rechargeable or a biodegradable device, e.g., a depot. Furthermore, it is contemplated that administration may occur by coating a device, implant, stent, or prosthetic. In a specific embodiment, the pharmaceutical compositions of the invention are administered intravenously.

In some embodiments, the pharmaceutical composition of the invention may be administered as part of a combination therapy with other agents. Combination therapy refers to any form of administration combining two or more different therapeutic agents. In some embodiments, the second therapeutic agent is administered while the previously administered therapeutic agent is still effective in the body (e.g., the two therapeutic agents are simultaneously effective in the patient, which may include synergistic effects of the two compounds). For example, the different therapeutic agents may be administered as a part of the same formulation or as separate formulations, either simultaneously or sequentially.

For example, the pharmaceutical compositions of the invention may be administered in combination with at least one other known antibiotics. The pharmaceutical composition of the invention and the at least one other known antibiotic may be administered sequentially or substantially at the same time. Varying the antibiotic may be helpful in reducing the ability of the pathogen, e.g., a bacterium, to develop resistance to TXB or the other known antibiotic, or to both. Non-limiting examples of other known antibiotics that may be administered in combination with the pharmaceutical compositions of the present invention include penicillins (e.g., natural penicillins, penicillinase-resistant penicillins, antipseudomonal penicillins, aminopenicillins), tetracyclines, macrolides (e.g., erythromycin), lincosamides (e.g., clindamycin), streptogramins (e.g., Synercid), aminoglycosides, and sulfonamides. In some embodiments, the pharmaceutical compositions of the invention may be administered in combination with compounds that target virulence factors such as, but not limited to, phenol-soluble modulins. In other embodiments, the pharmaceutical compositions of the invention may be administered in combination with compounds that target the efflux pumps of the pathogens.

The present invention is further illustrated by the following examples which should not be construed as limiting. The contents of all references, patents and published patent applications cited throughout this application are expressly incorporated herein by reference in their entirety.

EXAMPLES

Example 1. Identification of Pegylated Phospholipids (PPLs) as Vehicles for Use in a Pharmaceutical Composition of TXB The purpose of this study was to identify vehicles suitable for including in a pharmaceutical composition of TXB that prevent or significantly reduce gelation of TXB in serum. To this end, over 1,000 Generally Regarded as Safe (GRAS)

and FDA-approved vehicles and vehicle combinations were screened. The vehicles were structurally diverse. Table 1 lists the exemplary screened vehicles.

TABLE 1

Exemplary screened vehicles.

| Compound Class | Vehicle |
|---|---|
| Water-miscible solvents | PEG 300 |
| | PEG 400 |
| | Ethanol |
| | Propylene glycol |
| | Glycerin |
| | N-methyl-2-pyrrolidone |
| | Dimethylacetamide |
| | DMSO |
| | Transcutol HP |
| Cyclodextrins | Alpha-cyclodextrin |
| | Beta-cyclodextrin |
| | 2-hydroxypropyl-beta-cyclodextrin |
| | Captisol |
| Proteins and amino acids | Albumin |
| | Glycine |
| | Arginine |
| | Aspartic acid |
| | Glutamic acid |
| | L-methionine |
| Emulsifying agents | Cremophor EL |
| | Cremophor RH40 |
| | D-alpha-tocopheryl polyethylene glycol 1000 succinate (TPGS) |
| | Polysorbate 20 |
| | Polysorbate 80 |
| | Polysorbate 60 |
| | Macrogol 15 |
| | Hydroxystearate |
| | Sorbitan monooleate |
| | Poloxamer 407 |
| | Mono-fatty acid ester of PEG 300 |
| | PEG 500 mono-oleate |
| | Polyoxyl 40 stearate |
| | PEG 400 monooleate |
| | PEG 400 di-oleate |
| | Pluronic F-127 |
| | Pluronic 105 |
| | Pluronic F68 |
| | Brij10 |
| | BrijL4 |
| | Brij L23 |
| Sugars/Polysaccharides | Sucrose |
| | Hydroxypropyl cellulose |
| | Hydroxyethyl starch |
| | Sodium starch glycolate |
| | Sodium caproyl hyaluronate |
| | Sodium oleyl hyaluronate |
| Anionic polymers and salts | Poly-L-asparagine |
| | Poly-L-glutamic acid |
| | Sodium decanoate |
| | Sodium deoxycholate |
| | Pamoic acid disodium |
| PEG-lipids | 18:0 PEG2K PE |
| | 18:1 PEG2K PE |
| | 16:0 PEG2K PE |
| | 14:0 PEG2K PE |
| | 18:1 PEG5K PE |
| | 16:0 PEG550 PE |
| Miscellaneous | Povidone |
| | Sodium citrate |
| | Guanidine hydrochloride |
| | D-lactose monohydrate |
| | Citric acid monohydrate |
| | Tyloxapol |
| | Cholesterol |
| | Oleic acid |
| | PMAL-C8 |
| | Amphipol A8-35 |
| | PEG 1000 |
| | PEG 10000 |

FIG. 1 is a schematic illustration of the procedure used to screen the vehicles. As a first step, the vehicles were screened for their ability to solubilize TXB. Subsequently, TXB gelation and precipitation in rabbit serum was monitored using stereoscopic image detection and zetasizer analysis. Finally, in vitro and in vivo assays with mice and rabbits were used to narrow down the list of suitable vehicles for TXB.

Pegylated Phospholipids (PPLs) were identified as the lead vehicle candidates for the TXB formulation. FIG. 2 shows the names and structures of exemplary PPLs in the form of ammonium salt.

Example 2. Characterization of an Exemplary Pharmaceutical Composition of TXB An exemplary pharmaceutical composition comprising TXB was prepared with a PPL and is being referred to hereinafter as "TXB-PPL". In this pharmaceutical composition, TXB did not noticeably gelate when added to serum at the concentration of up to 2000 μg/mL. This is greater than about 25-fold improvement over the previous best formulation TXB, when tested as a part of TXB-PPL, had a MIC against MRSA OF 0.25 μg/mL and against *M. tuberculosis* strains of 0.125 μg/mL. This indicates that TXB did not lose its antibacterial potency when formulated with PPL. In this pharmaceutical composition, TXB also bound lipid II and lipid III, consistent with the mechanism of action described in Ling et al., Nature 2015, 517:455-459.

In vivo screens of TXB-PPL were performed in a CD-1 mouse sepsis model by intravenous administration into the tail vein. The maximum tolerated dose (MTD) of TXB-PPL was determined to be at least 50 mg/kg. This is about 5 times greater than the MTD of TXB dissolved in water (TXB-water). Preliminary pharmacokinetics (PK) studies have been performed in mice to compare the blood levels of TXB-PPL to free TXB (TXB-water). In the first study, a single dose of 20 mg/kg of TXB in PPL was administered intravenously, and the concentration of TXB in circulation was measured over 8 hours after the injection. In the second study, a single dose of 50 mg/kg of TXB in PPL or multiple consecutive doses of 50 mg/kg TXB in PPL over 5 days were administered intravenously, and the concentration of TXB in the circulation was measured over 8 hours after the injection.

Table 2 shows various pharmacokinetic parameters determined in the experiment.

TABLE 2

Pharmacokinetic parameters after a single injection of TXB-PPL or TXB-water.

| Pharmacokinetic Parameter | TXB-water | TXB-PPL |
|---|---|---|
| Concentration of TXB at 0.5 hours after injection (μg/mL) | 7.60 | 80.7 |
| Concentration of TXB at 8 hours after injection (μg/mL) | 0.07 | 0.35 |
| AUC (μg*hr/mL) | 28.2 | 157.6 |
| Half-life (hr) | 0.90 | 0.98 |
| Clearance (mL/min/kg) | 11.8 | 2.11 |

Figure 3:
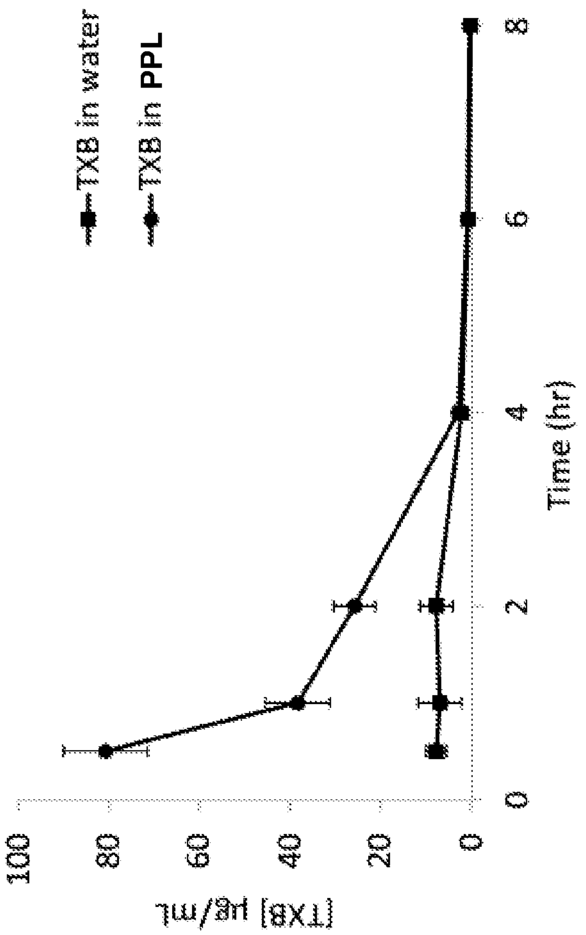
FIG. 3 is a graph showing the concentration of TXB in the circulation over time for TXB-PPL and TXB-water.

FIG. 3 is a graph showing the concentration of TXB in the circulation over time for TXB-PPL and TXB-water. The results shown in Table 2 and FIG. 3 indicate that 0.5 hours after injection, TXB concentration in the circulation is about 11-fold higher after injection of TXB-PPL than after injection of TXB-water. The results also indicate that injection of TXB-PPL results in TXB levels in the circulation that are higher than the minimum inhibitory concentration (MIC) for *M. tuberculosis* for up to 8 hours.

Figure 4:
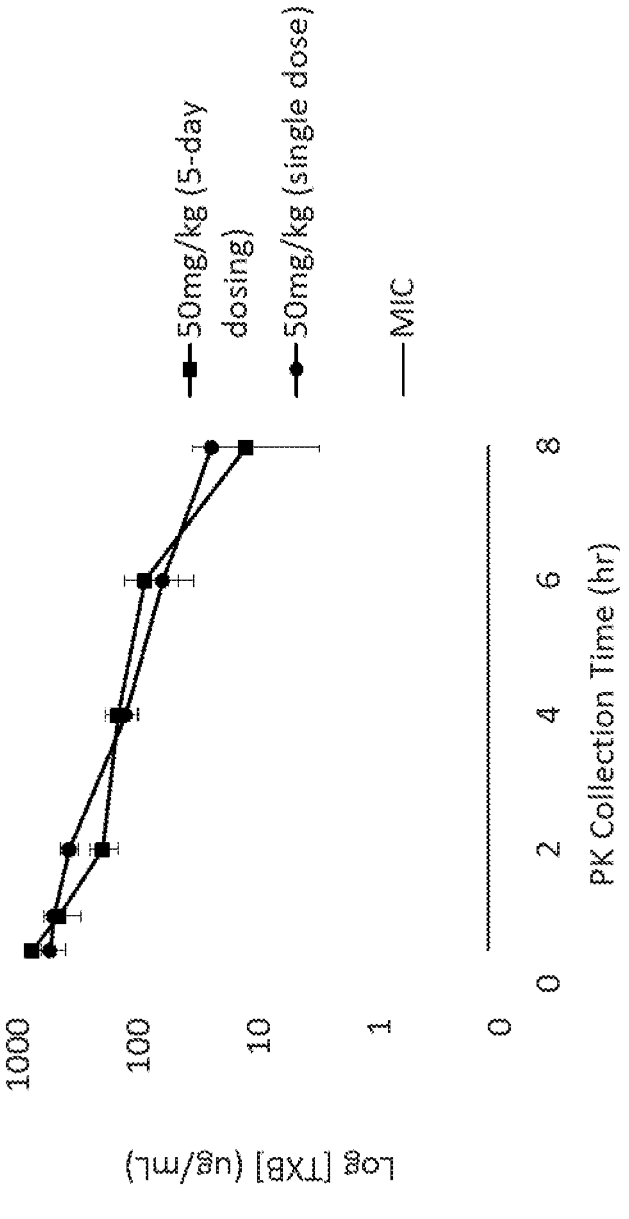
FIG. 4 is a graph showing the concentration of TXB in the circulation in CD-1 mice up to 8 hours after a single dose or 5 days of consecutive dosing of TXB in PPL.

FIG. 4 is a graph showing the concentration of TXB in the circulation up to 8 hours after a single dose or 5 days of consecutive dosing of TXB in PPL. The results indicate that in case of for both a single and multiple TXB doses, the concentration of TXB in the circulation remains at a level which is about 100-fold higher than MIC.

Figure 5:
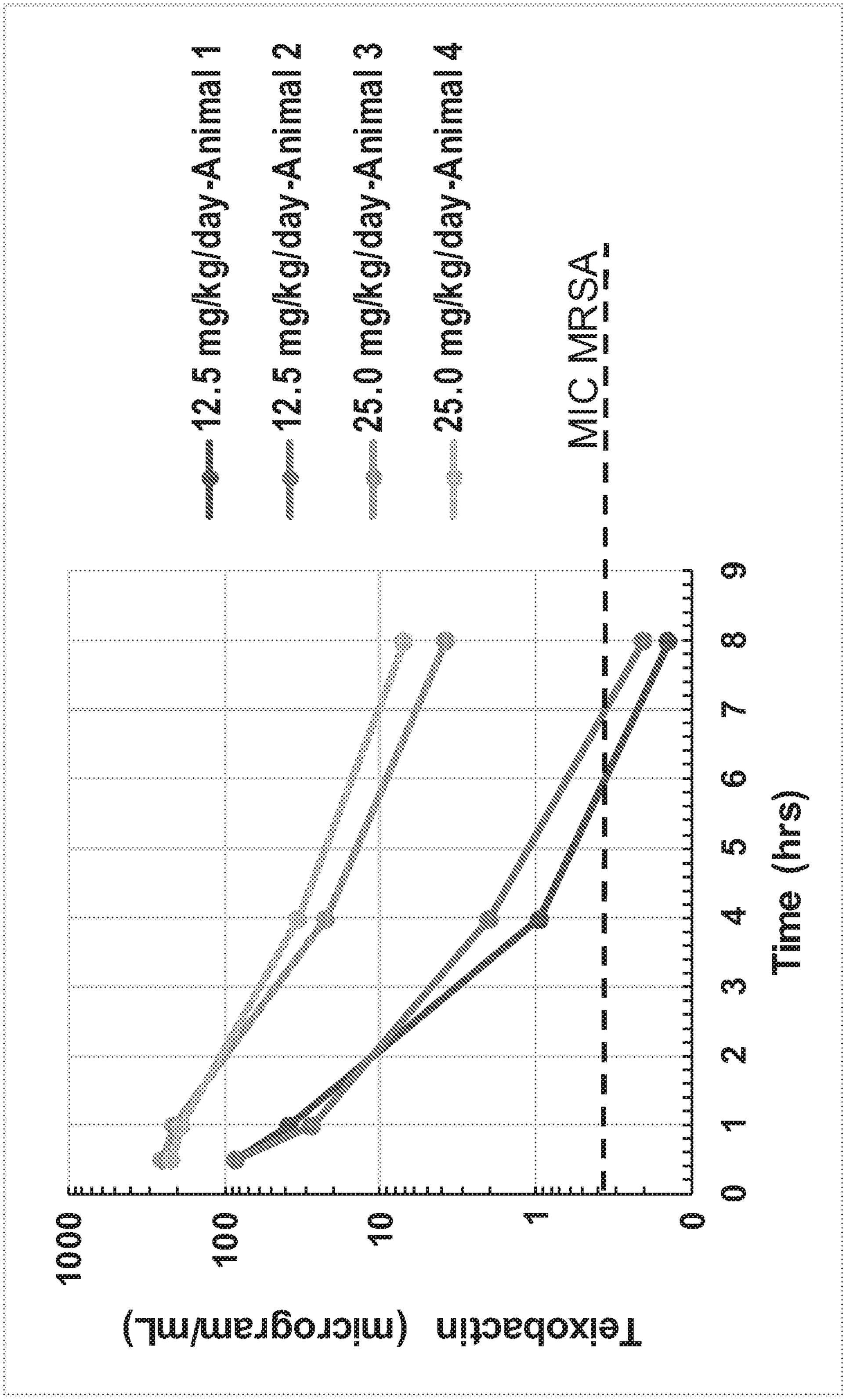
FIG. 5 is a graph showing the concentration of TXB in the blood of Sprague-Dawley rats over 8 hours after administration of 12.5 mg/kg/day or 25.0 mg/kg/day doses of TXB-PPL.

In addition, a five-day tolerance and PK study using TXB-PPL was performed using Sprague-Dawley rats. The rats received TXB doses of 12.5 mg/kg/day and 25 mg/kg/day, which are higher than the maximum tolerated dose (MTD) achieved using previous TXB compositions, e.g., a composition of TXB comprising 20% captisol and 5% dextrose. Concentration of TXB in the blood was measured over 8 hours after administration of the fifth (final) dose. FIG. 5 is a graph showing the concentration of TXB in the blood of Sprague-Dawley rats over 8 hours after administration of 12.5 mg/kg/day or 25.0 mg/kg/day doses of TXB-PPL. The results shown in FIG. 5 indicate that the concentration of TXB in the blood remains well above the MIC for MRSA for several hours. There were no adverse effects observed with either dose. Also, there was little or no detectable TXB in the sample taken just prior to dosing on Day 5, indicating there was insignificant accumulation of TXB in the blood over the four-day period.

A five-day tolerance and PK study was next performed in New Zealand white rabbits, using TXB-PPL and the TXB doses of 10 and 20 mg/kg/day. Both doses were well tolerated over the 5-day period, and two animals were injected with each dose. The concentration of TXB in the blood was measured over 24 hours after administration of the fifth (final) dose and various pharmacokinetic parameters were determined. Table 3 shows various pharmacokinetic parameters determined in the experiment.

TABLE 3

Pharmacokinetic parameters after 5 injections of TXB as TXB-PPL at the dose 10 mg/kg/day or 20 mg/kg/day in rabbits.

| Pharmacokinetic Parameter | Dose (mg/kg/day) 10 | 20 |
|---|---|---|
| Cmax (μg/mL) | 165 | 382 |
| AUC to last (μg*hr/mL) | 115 | 262 |
| $T_{1/2}$ (hr) | 3.5 | 2.8 |
| Vol (mL/kg) | 70.6 | 53.5 |
| Clearance (mL/hr/kg) | 38.5 | 17.4 |

Figure 6:
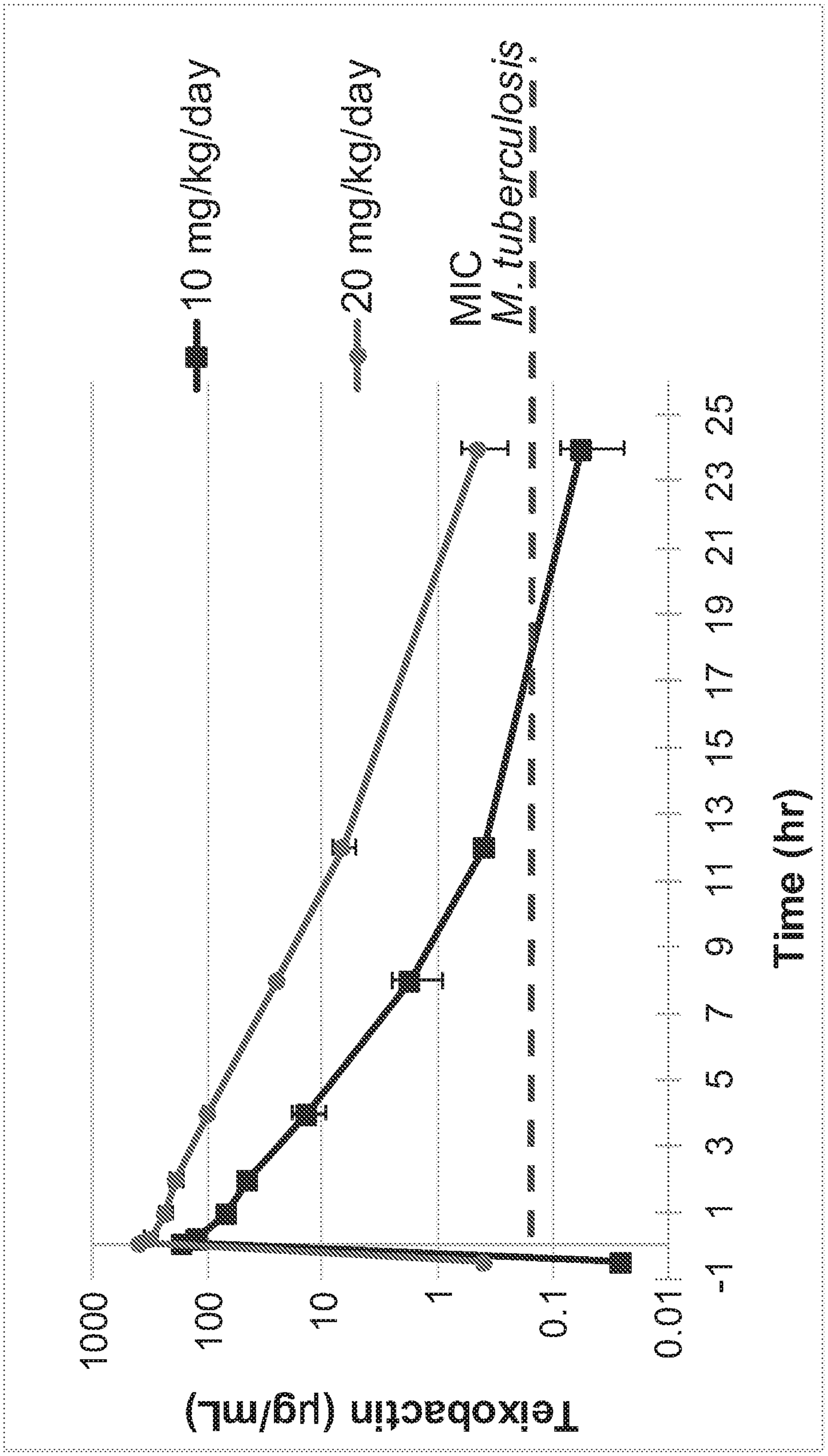
FIG. 6 is a graph showing the concentration of TXB in the blood of New Zealand White rabbits over 24 hours after administration of 10 mg/kg/day or 20 mg/kg/day doses of TXB-PPL.

FIG. 6 is a graph showing the concentration of TXB in the blood of rabbits over 24 hours after administration of 10 mg/kg/day or 20 mg/kg/day doses of TXB-PPL. The results shown in Table 3 and FIG. 6 indicate that the concentrations of TXB remained well above the MIC for *M. tuberculosis* for over 12 hours after repeated administration of the 10 mg/kg/day dose, and over 24 hours after repeated administration of the 20 mg/kg/day dose. The PK parameters were approximately dose proportional. In comparison, rabbits were not able to tolerate multi-day injections of older formulations of TXB, e.g., TXB formulation comprising 5% dextrose (D5W) or a TXB formulation comprising 20% captisol and D5W, at the concentration of TXB of 5/mg/kg/day. Thus, TXB-PPL is better tolerated than TXB in D5W or TXB in.

Example 3. In Vivo Efficacy of an Exemplary Pharmaceutical Composition of TXB TXB-PPL was next tested in two mouse models of infection to ensure that the efficacy of TXB was not adversely affected when it was formulated with PPL. TXB-PPL was first tested in a standard mouse sepsis protection model, which provides preliminary efficacy information indicating good systemic exposure. The model determines a compound dose that results in 50% survival ($PD_{50}$) of infected mice after 48 hours post-treatment. The infection agent was a commonly-used clinical isolate, *S. aureus* MRSA ATCC 33591. Female CD-1 mice were infected with 0.5 mL of bacterial suspension ($3.28\times10^7$ CFU/mouse) by intraperitoneal injection, a concentration that achieves at least 90% mortality within 48 hours after infection. At one-hour post infection, TXB was administered intravenously as a part of TXB-PPL in an escalating single dose, using a dose volume of 10 mL/kg. TXB showed an excellent $PD_{50}$ of 0.24 mg/kg, which is similar to a previously determined value of 0.19 mg/kg (Ling et al., Nature 2015, 517:455-459).

The second study used a neutropenic mouse thigh infection model infected with MRSA ATCC 33591. This model is useful for measuring the effect of a drug on the pathogen with most of the host immune system eliminated. This model is also useful for determining pharmacokinetic/pharmacodynamic (PK/PD) parameters to estimate dosing in humans. Finally, this is also a good model for acute bacterial skin and skin structure infections (ABSSSI), a potential clinical indication for TXB. Female CD-1 mice (5 mice per group) were rendered neutropenic by cyclophosphamide, administered in two consecutive doses of 150 and 100 mg/kg 4 and 1 day prior to infection. Bacteria were injected into the right thighs at $2.8\times10^5$ CFU/mouse. At 2 hours post infection, mice were intravenously administered a single dose of TXB as TXB-PPL at the dose volume of 10 mL/kg. Two groups of mice acted as the infected but untreated control groups. At 2 hours post infection, one group of infected but untreated mice was euthanized and the right thighs aseptically removed, weighed, homogenized, serially diluted, and plated on trypticase soy agar. After 48 hours, the colonies were counted to quantify the colony forming units (CFU) per gram of thigh tissue at the time of treatment. At 26 hours post infection, the remaining mice (treated and untreated control group) were euthanized and the right thighs processed as described above.

Figure 7:
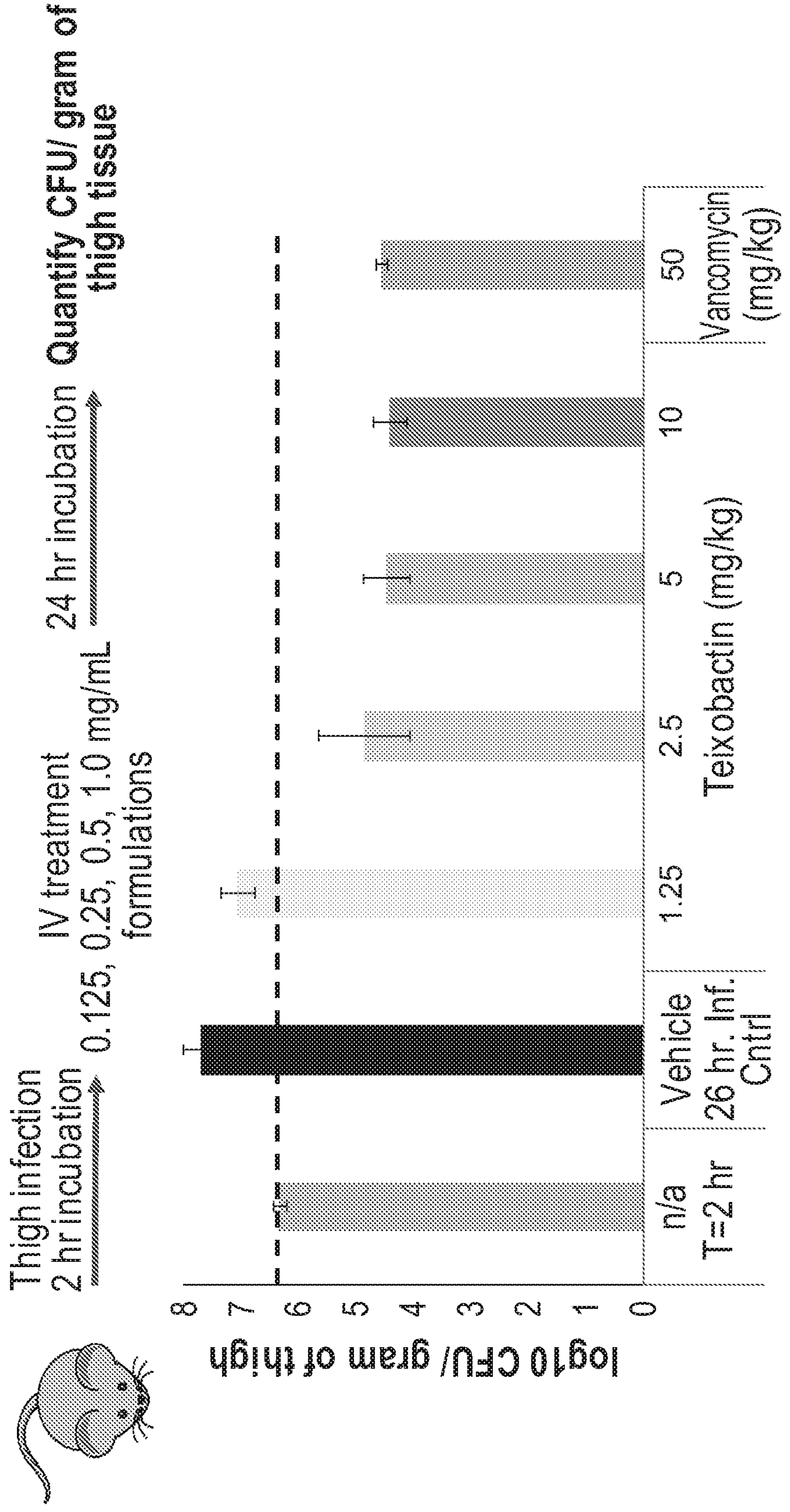
FIG. 7 is a bar graph showing $log_{10}$ CFU per gram of thigh tissue for various treated and untreated groups. Bar graph labeled "n/a" corresponds to infected but untreated control group at 2 hours post infection. Hashed line indicates infection level at time of dosing.

FIG. 7 is a bar graph showing $\log_{10}$ CFU per gram of thigh tissue for various treated and untreated groups. Bar graph labeled "n/a" corresponds to infected but untreated control group at 2 hours post infection. Hashed line indicates infection level at time of dosing.

The results shown in FIG. 7 indicate that TXB administered as part of a TXB-PPL based pharmaceutical composition as a single intravenous dose of greater than 2.5 mg/kg significantly reduced pathogen load. TXB treatment results in a 3-log reduction in CFU compared to vehicle control. These results favorably compare to vancomycin, as well as to the recently approved drugs Orbactiv® (oritavancin), which has an effective dose of 4-5 mg/kg.

The studies indicate that, when TXB is formulated with PPL, the serum gelation issue is eliminated or significantly reduced without any loss in bioactivity.

Example 4. Additional In Vitro and In Vivo Pharmacokinetics (PK) and Safety Pharmacology Studies Using an Exemplary Pharmaceutical Composition of TXB Animal species for use in the studies. Commonly, male animals are used in the non-GLP and GLP safety pharmacology studies to reduce variability. However, both males and females are used in the toxicity studies to take into consideration gender differences. Crl:CD® Sprague-Dawley rats (from Charles River Lab), weighing about 250 grams and of the age of about 7 to 8 weeks old are used as the rodent species for PK, biodistribution, elimination, safety pharmacology and toxicity studies. Beagle dogs (from Marshall BioResources), weighting 6-12 kg and of the age of 7-15 months are used as the non-rodent species for safety pharmacology and toxicity studies. Other species (e.g., cynomolgus monkeys) are used for the studies if in vitro metabolic profiling indicates other species may be more relevant for humans.

New Zealand white rabbits (from Covance, Denver, PA) weighing 2.2 to 2.6 kg, pathogen-free, female, non-pregnant is a preferred species for testing efficacy in treating TB infection. This species forms lung granulomas after aerosol exposure to *M. tuberculosis*, similar to the disease progression in human. The number of lung lesions and the pathogen load allow the quantitation of efficacy of test antibiotics.

Mice are the rodent of choice for PK/PD studies. Mice have a long history of being the lowest phylogenetic species that provide a good model for human bacterial infections. The study uses pathogen free ICR (CD-1) mice (from Charles River Laboratories), non-pregnant females, about 6 weeks old, weighing 20-25 grams. Mice are also desirable for this study because bacterial infection in mice is highly reproducible and the thighs can be easily removed for exact quantitation of bacteria. Female mice are used in the study because a large number of animals is needed for the study, and males may fight and elicit stress response when caged together. Also, female mice are more easily infected with MRSA, and the resulting data takes into account variability due to estrous cycles.

Animal numbers. The number of animals used in each proposed experiment is the minimum number of animals required to obtain scientifically valid results, taking into consideration inter-individual variability in PK, efficacy and toxicity parameters. Conventionally accepted values are applied for: 1) "statistical power" set at 0.8 (80% probability that a treatment effect is detected if present), and 2) "p level" set at 0.05 (5% probability that a significant difference occurs by chance).

For the following animal studies TXB formulated with PPL is administered intravenously to the animals. The dose of TXB for each animal is calculated based on the most recent body weight. The age and weight of the animals within each study is as uniform as possible. The pharmacokinetic (PK), safety pharmacology and PK/PD studies include: single-dose PK study in rats; PK dose ranging study in rats; multiple dose PK evaluation in rats; biodistribution study in rats; elimination study in rats; PK/PD study in mice; cardiac safety pharmacology study to evaluate cardiac function and electrophysiology in dogs; CNS safety pharmacology study in rats; and respiratory safety pharmacology in rats. The toxicity studies include: acute dose range-finding toxicity study and 7 days repeated-dose study in rats; acute dose range-finding toxicity study and 7 days repeated-dose study in dogs; 28-day toxicity study and recovery period in rats; 28-day toxicity study and recovery period in dogs; and genotoxic potential study in mice. For studies involving repeated dosing and multiple blood sampling, the animals (rats and dogs) surgical implantation of jugular cannulae and femoral vein catheters is used to facilitate blood sampling and dosing.

Example 5. Pharmacokinetic (PK) and Pharmacokinetic/Pharmacodynamic (PK/PD) Studies to Characterize the In Vivo Disposition of TXB The goal of the studies is to characterize the in vivo disposition of TXB formulated with PPL in the rat as a standard rodent model for PK and drug disposition. In addition, metabolic profiling in liver microsomes from multiple species is performed to identify any major metabolite production.

Single dose PK study. This study evaluates the systemic exposure, residence time including terminal half-life and systemic exposure of TXB. The study uses 6 male rats, and the administered dose is 0.5 MTD. Blood is collected from 3 rats per timepoint for 8 timepoints (e.g., pre-dose; at 5 and 30 minutes; and at 1, 2, 4, 8, and 12 hours post-dose). Animals are rotated for blood collection, and approximately 0.1-0.2 mL of blood is collected in potassium EDTA tubes. The whole blood samples are centrifuged at ~1500×g for a minimum of 10 minutes in a refrigerated centrifuge at 4° C. Plasma is transferred within 30 minutes of blood collection and centrifugation to labeled tubes, and the tubes are frozen and stored in the dark at −80° C. until analysis of TXB level by LC-MS. The maximum (initial for IV) peak plasma concentration ($C_{max}$), the plasma terminal half-life ($t_{1/2}$) and the area under the plasma concentration time curve (AUC) is calculated from the plasma concentration data. The clearance and volume of distribution is determined from the concentration-time profiles by standard noncompartmental analysis.

PK dose ranging study. To assess the dose-dependency of PK parameters and dose-proportionality of systemic exposure, 24 male rats are administered single, escalating doses of TXB intravenously, and plasma drug levels are monitored over time. The dose levels of TXB depend on the results of the single dose evaluation. Up to 4 dose levels are tested, with the MTD being the highest dose. The dose ranging study is essential in selecting an appropriate dose level for further studies that ensures sufficiently high levels (several times MIC) of drug concentrations. Blood is collected from 3 rats per timepoint for 8 timepoints (e.g., pre-dose; at 5 and 30 minutes; and at 1, 2, 4, 8, and 12 hours post-dose) for PK analysis and processed as described above. Comparison of PK parameters between different doses also provides information about dose-linearity and dose-dependency, interindividual variability and absorption profiles and mechanisms. Descriptive statistical analysis, as well as one-way analysis of variance with posthoc Tukey test, is performed to identify differences in parameters between the treatment groups.

Multiple dose PK evaluation. The extent of drug accumulation and potential auto-induction or inhibition of clearance pathways is assessed in a multiple dose PK evaluation. The study uses 12 male rats that are administered 10 consecutive IV doses of TXB. The dose and time interval are determined by the results of the single dose evaluation. Blood is collected from 3 rats per timepoint for 8 timepoints (e.g., pre-dose; at 5 and 30 minutes; and at 1, 2, 4, 8, and 12 hours after the last dose). If adverse effects are noted with consecutive doses, the dose is decreased. Blood samples are drawn at time points after the first and the last dose of the series, with one sample taken just before the last dose to assess any accumulation. Sample processing and analysis is performed as described above.

Biodistribution study. LC-MS is used to quantitate TXB and any major metabolites in biological samples (liver, lungs, heart, kidney, brain, spleen, urine, feces). Depending on the biological source, sample preparation includes, if necessary, tissue homogenization, organic extraction, and column chromatography. To assess the basic biodistribution and organ/tissue accumulation of TXB, 5 male rats are administered a single IV dose of TXB every 8 hours for 10 consecutive doses. The dose is the same as in the multiple dose PK evaluation. One hour after the final dose, animals are sacrificed and all major organs (liver, lungs, heart, kidney, brain, and spleen) are harvested, frozen in liquid nitrogen and stored at −80° C. until homogenization. Tissues are analyzed for total and free drug level, and any major metabolites of TXB.

Elimination study. The goal of this study is to assess the major metabolic and elimination pathways of TXB. In the study, 5 male rats are administered a single IV dose of TXB at the MTD. Urine samples are collected pre-dose; at intervals of 0 to 8 hours and 8 to 24 hours; and at 24 hour intervals through 48 hours. Fecal samples are collected pre-dose and at 24-hour intervals for up to 48 hours after the dose. The animals are transferred to new cages at the end of each collection intervals. Samples are stored frozen at −20° C. until analysis. The samples are analyzed by LC-MS for the parent TXB and any major metabolites.

Metabolic profiling. The goal of this study is to determine whether a significant amount of a TXB metabolite may be produced in a mouse, a rat, a dog, a monkey or human and to help confirm the selected species for the in vivo studies. Based on the FDA recommendations, a metabolite present at ≥10% of the original compound is considered to be significant. If it is established that a significant metabolite is specific to humans, the metabolite is included in subsequent in vivo pharmacology and animal toxicity studies.

The metabolic stability of TXB is tested in mouse, rat, dog, monkey and human pooled liver microsomes, S9 and cytosolic preparations to capture metabolism by the cytochrome P450 mixed function oxidation system as well as soluble cytoplasmic phase II enzymes. Briefly, mouse, rat, dog, monkey and human pooled liver microsomes, S9 and cytosolic preparations are incubated with TXB at 37° C. After termination of the reaction, the supernatant is separated from the subcellular preparations by centrifugation and metabolites are isolated and characterized by LC-MS.

PK/PD in neutropenic mouse thigh model. The standard neutropenic mouse thigh model is used to conduct PK/PD studies to determine the rate of bactericidal activity at increasing doses. Pathogen free ICR (CD-1) mice are rendered transiently neutropenic by intraperitoneal injections of cyclophosphamide 4 days at the dose of 150 mg/kg) and 1 day at the dose of 100 mg/kg prior to infection. The bacterial strain *S. aureus* ATCC 33591 (MRSA) is cultured in Mueller-Hinton (MH) broth to an absorbance of 0.3 at 580 nm. The culture is diluted 1:10 in MH broth and aliquots of the dilutions are plated on MH agar plates to determine the actual number of CFU delivered. A total of 106 bacteria (0.1 mL inoculum) is injected directly into the thighs of halothane-anesthetized mice. The study uses a total of 169 mice and is divided into two parts as described below.

For pharmacokinetic studies (Part 1), the thigh-infected animals are administered single IV doses of TXB (up to 3 concentrations). Blood is removed from 3 mice per timepoint per dose at 5 minutes, 30 minutes and 1, 2, 4, 8 hours via cardiac puncture while under $CO_2/O_2$ anesthesia, and plasma TXB levels (total and free) are measured. PK calculations are performed using WinNonlin (Pharsight Corp) by non-compartmental analysis. Integrating the PK parameters with the MIC provides three PK/PD parameters which quantify the activity of an antibiotic: the Peak/MIC ratio ($C_{max}$ divided by the MIC), the T>MIC (time above MIC which is the percentage of a dosage interval in which the serum level exceeds the MIC), and the 24 hour AUC/MIC ratio (the 24 hour AUC divided by the MIC). A total of 54 mice are used in the study (3 TXB concentrations*6 timepoints*3 mice per timepoint).

To determine which PK/PD parameter best correlates with efficacy (Part 2), mice are treated with TXB via IV dosing two hours post infection with 20 different dosing regimens using two-fold increasing total doses divided into one, two, four or six doses. The thighs are harvested from untreated control animals at the time of infection, time of treatment and 26 hours post-infection, and from treated animals after 24 hours of therapy. The thighs are weighed, homogenized in saline and plated on MHA agar for CFU determination. Non-linear regression analysis is used to determine which PK/PD parameter(s) best correlates with efficacy. A total of 115 mice is used in the study (20 dosing regimens*5 mice per group+5 untreated mice immediately after infection+5 untreated mice at time of treatment+5 untreated mice at 26 hours post-infection).

The plasma concentration of TXB and the CFU per thigh is calculated per treatment dose. The data is used to analyze the relationship between the dose level, the plasma concentration of TXB and the change in CFU/thigh in infected mice.

Example 6. Safety Pharmacology (GLP)

This set of studies is aimed at characterizing the pharmacological safety of TXB.

Interaction with enzyme and receptor panels. In vitro pharmacology tests are aimed at identifying possible side effects of TXB and its major metabolite, if present. Specifically, if it is found that TXB interacts with a certain enzyme or a receptor, then close attention is paid to the relevant function of the enzyme or receptor in toxicity studies, and additional procedures examining the function are implemented. The possible effects of TXB in vitro on a panel of enzymes which are useful markers of potential adverse events are evaluated. Such exemplary tests include assays for fundamental metabolic enzyme inhibition (ATPase, carnitine transferases, nitric oxide synthase, various peptidases, serine/threonine kinases) and activity at receptor sites that are involved in basic physiology (adenosine, various neurotransmitters, calcium and sodium channels). TXB is tested at concentrations that range from 10 to 1,000× of the level of TXB in serum at which good animal efficacy is observed. In each of these in vitro assays, a positive control is included that provokes a 50% response or binding to the target.

Cardiac safety pharmacology: cardiac function and electrophysiology in vivo. This study is aimed at examining the entire cardiac cycle at both the hemodynamic and electrophysiological levels. The study uses 4 male dogs are surgically implanted with telemetry probes to measure the following parameters: arterial blood pressure waveforms (systolic, diastolic, pulse and mean); heart rate (derived from the arterial waveform); ECG waveforms (PR, QRS, RR, QT, and QTc intervals); and body temperature. Each animal is administered a vehicle control and three intravenous dose levels of TXB using a Latin square dose design with a washout period between doses. Three doses are chosen with the MTD as the top dose, along with a middle and low dose. On dosing days, a 60 mute baseline is recorded for each parameter prior to TXB administration. Telemetry data is collected for no less than 24 hours. An estimate of the No Observed Adverse Effect Level (NOAEL) is made. The NOAEL is the greatest amount of a substance which causes no detectable adverse alteration of the studied function and should be at least 10× higher than the dose that is initially administered to humans.

CNS safety pharmacology. The goal of this study is to evaluate any adverse neurobehavioral effects in 40 male rats following IV administration of three dose levels of TXB and a vehicle control. The animals are randomly split into four groups (10 rats per group), one dose per group. The doses are chosen with the MTD as the top dose, a middle dose, a low dose, and a vehicle-only control. Motor activity is measured prior to dosing and at time approximating peak blood concentrations, using Opto-Varimex (Columbus Instruments) activity monitoring boxes. A functional observational battery (FOB) is conducted prior to dosing and at one time (approximately 60 minutes) post-dosing. The functional observational battery is comprised of four sets of observations. The first set of observations (posture, involuntary motor movement, biting, palpebral closure and vocalizations) is performed while the animal is in its home cage. The second set of observations (ease of removing animal from cage, ease of handling animal, lacrimation, color of tears, salivation, piloerection, appearance of fur, palpebral closure, exophthalmos, respiration) is performed when initially handling the animal. The third set of observations (mobility, posture, involuntary motor movements, gait abnormalities, arousal reactivation to environment, stereotypical behavior such as any repetitive action, bizarre behavior, number of rears, defecation, urination and vocalizations) is performed in a test arena. The fourth set (approach response, touch response, auditory response, tail pinch response, eye blink response, righting reflex, hind limb extensor strength response, pupillary size, body weight) is comprised of handling/specific testing of the animal. Each animal is scored to assess the impact of TXB on the CNS.

Respiratory Safety Pharmacology. An additional regulatory requirement for safety pharmacology includes a study of respiratory function. The study uses 16 male rats that are acclimated for several days prior to start of study. On the study day, the animals are randomly split into four groups (4 rats per group), one dose per group. The doses are chosen with the MTD as the top dose, a middle dose, a low dose, and a vehicle-only control. On the study day, the head and neck of the animal is sealed into a plethysmograph chamber. All data acquisition and calculations are performed by a BUXCO Pulmonary Mechanics Computer. The animals are allowed to stabilize in the chamber for a minimum of 1 hour prior to test article administration, and data collected pre-dosing. Following TXB or vehicle-only administration, data is collected for 5 hours. Only one dose level is administered to each animal. The following parameters are recorded or calculated and reported: respiratory rate, tidal volume and minute volume. Two 15-minute pre-dose intervals are calculated and reported for the baseline. Post-dose data is grouped in 15-minute intervals to calculate means, and the data is analyzed to examine the influence of TXB on respiratory function. A lack of toxicity is judged as no statistically or clinically significant (>25%) functional changes.

Example 7. Toxicity Studies

The toxicity studies are conducted in rats and dogs to identify the maximum tolerated dose (MTD) defined as the dose that does not produce mortality, more than a 10% decrement in body weight, or overt clinical signs of toxicity, and to identify the repeated dose MTD over a period of one week. The study is composed of two phases (Phase A and Phase B) for both species. In Phase A, the single dose level is increased until the maximum tolerated dose (MTD) is determined. In Phase B, animals are dosed daily for 7 days at fractions of the single dose MTD to estimate a repeat dose MTD. Detailed physical examinations, body weight and food consumption measurements are made daily. Necropsy is performed on all animals that are found dead, euthanized in extremis or at the scheduled necropsy. The route of administration is IV.

Acute dose range-finding toxicity and 7 days repeated-dose study in rats (non-GLP). In Phase A, animals are randomized into groups (3 male and 3 female rats per group). The animal number breakdown is shown in Table 4.

TABLE 4

Animal number breakdown for acute dose range-finding toxicity (Phase A) and 7 days repeated-dose (Phase B) in rats (R) and dogs (D).

Phase A

| | MTD Determination | |
|---|---|---|
| | Males (R/D) | Females (R/D) |
| Dose Level 1 | 3/1 | 3/1 |
| Dose Level 2 | 3/a | 3/a |
| Dose Level 3 | 3/a | 3/a |
| Dose Level 4 | 3/a | 3/a |

Phase B

| | Repeated Dose MTD Main Study | | Toxicokinetics (TK) | |
|---|---|---|---|---|
| | Males (R/D) | Females (R/D) | Males (R) | Females (R) |
| Control | 5/2 | 5/2 | 0 | 0 |
| 0.25 MTD | 5/2 | 5/2 | 9 | 9 |
| 0.5 MTD | 5/2 | 5/2 | 9 | 9 |
| MTD | 5/2 | 5/2 | 9 | 9 |

Each group is given an ascending dose until the maximum tolerated dose (MTD) is determined. Up to 4 doses of TXB are tested, and the animals are sacrificed 24 hours after dosing. Determining the single-dose, acute MTD allows to choose the top dose in repeat dosing studies (Phase B).

In Phase B, the repeat-dose segment (7 days, once daily dosing) is conducted with three dose levels: the single dose MTD, 0.5 MTD and 0.25 MTD and a control group receiving the vehicle only. In addition, there are satellite groups for toxicokinetic (TK) analyses to permit its correlation with any toxicity that is found. These groups consist of animals receiving TXB at the same doses as in the main study, and be used to collect blood samples at various time points after the last dose on the seventh day. Clinical signs and mortality check are made twice daily on all animals. Cage-side observations are made once daily. Detailed observations are made once during the pre-dose phase, on Days 1, 3, and 7 of the dosing phase and on the day of necropsy. Food consumption (quantitative, by cage) is measured on days 1-3, 3-7, and body weights are taken once during the pre-dose phase, days 1, 3 and 7, and on the day of necropsy. Blood samples are analyzed for test material content and pharmacokinetic parameters ($C_{max}$, $T_{max}$, T, AUC, CL, Vol). Termination of repeat-dose animals is 24 hours after the last dose with pre-terminal clinical pathology (serum chemistry, coagulation and standard panel for hematology) and standard necropsy of macroscopic examination and tissue collection, organ weights (standard panel) and histopathology on all tissues for all animals.

Acute dose range-finding toxicity and 7 days repeated-dose study in dogs (non-GLP). For dogs, Phase A consists of ascending dosing of animals to determine maximum tolerated dose (MTD) for TXB (1 animal/sex/dose/day). The animal breakdown is shown in Table 4. To conserve animals, the same male and female dogs are exposed to each of 4 dose levels, with a "washout period" between doses for clearance of the drug prior to subsequent exposure.

This is followed by Phase B, the repeat-dose segment (7 days, once daily dosing) where the same animals are dosed at one dose level once daily for 7 days (2 animals/sex/dose). Up to 3 dose levels of TXB are tested, as well as a vehicle-only control. The body weight and cage-side observations (nature, onset, and duration of all gross or visible toxic or pharmacological effects) are recorded at 1, 2.5, and 4 hours post-dosing, and food consumption is measured for the duration of the treatment period.

Toxicokinetic analysis is conducted on blood samples collected following the first and last dose at 6-8 timepoints per animal. Samples are analyzed for test material content and the pharmacokinetic parameters ($C_{max}$, $T_{max}$, T, AUC, CL, Vol) are determined. The animals are terminated 24 hours after the last dose. Clinical pathology and gross necropsy are performed as described above for the rats.

The following studies are conducted to determine the long-term toxicity of TXB, using the same species, age and sex as in the 7-day study. These studies follow the general outline of the 7-day toxicity studies, but dosing is for 28 days after which all the animals are euthanized. An additional group of animals is kept under observation after the end of the dosing periods for an additional 28 days in order to assess any latent toxicity effects, and the rate of recovery from the previous dosing. Three dose levels plus a control group receiving the vehicle only are tested.

28-day toxicity study and recovery period in rats. Animals are randomized into groups as shown in Table 5.

TABLE 5

Animal number breakdown for a 28-day toxicity study and recovery period in rats.

| | Main Study | | Toxicokinetics (TK) | | Recovery | |
|---|---|---|---|---|---|---|
| | Males | Females | Males | Females | Males | Females |
| Control | 10 | 10 | 0 | 0 | 5 | 5 |
| Low Dose | 10 | 10 | 9 | 9 | 0 | 0 |
| Mid Dose | 10 | 10 | 9 | 9 | 0 | 0 |
| High Dose | 10 | 10 | 9 | 9 | 5 | 5 |

Three doses of TXB are tested, and the animals are dosed once daily for 28 days. The animals are checked twice daily for moribundity and mortality, undergo a weekly detailed clinical examination and are monitored for food consumption and body weights. Cage-side observations are recorded at 1, 2.5 and 4 hours after dosing daily with weekly detailed clinical examination. Food consumption and body weights are recorded once/day. Pre-study and pre-terminal ophthalmic exams are conducted on main study animals, and pre-terminal clinical pathology (serum chemistry, coagulation, hematology and urinalysis) is analyzed for all main study animals. The animals in the main study are terminated after 28 days of dosing, with complete gross necropsy and organ weights on all main study animals. Histopathology is done on control and high-dose main study animals for full tissue list (approx. 2,560 tissue samples total). Histopathology is done for affected organs in lower dose groups.

Satellite groups (9/sex per treated group) are similarly dosed and the blood is sampled for toxicokinetics, alternately sampled as 3 animals/sex/time point at six timepoints on first and last day of dosing. Samples are also taken from control group animals at a single timepoint on TK days. Plasma samples are analyzed for test material content, and the PK parameters ($C_{max}$, $T_{max}$, T, AUC, CL, Vol) are determined.

In addition, a group (5 male and 5 females per group) in the control and the high-dose groups are similarly dosed for 28 days and kept as 28-day recovery animals. Cage-side observations are performed daily. This set of animals is terminated 28 days after completion of treatment period with pre-terminal clinical pathology and ophthalmic examination, and histopathology on target tissues.

28-day toxicity study and recovery period in dogs. This study mimics the study for rats as described above, with additional ophthalmologic and electrocardiogram (ECG) exams performed pre-test and near the end of the dosing and recovery periods.

The animals are randomized into groups as shown in Table 6.

TABLE 3

Animal breakdown for 28-day toxicity study and recovery period in dogs.

| | Main Study | | Recovery | |
|---|---|---|---|---|
| | Males | Females | Males | Females |
| Control | 4 | 4 | 2 | 2 |
| Low Dose | 4 | 4 | 0 | 0 |
| Mid Dose | 4 | 4 | 0 | 0 |
| High Dose | 4 | 4 | 2 | 2 |

Three doses of TXB are tested, and the animals are dosed once daily for 28 days. Viability is checked twice daily. Cage-side observations are recorded at 1, 2.5 and 4 hours after dosing daily. The weekly detailed clinical examination includes daily body weights, daily food intake monitoring in dogs, pre-study and pre-terminal ophthalmic exams. Clinical pathology (serum chemistry, coagulation, hematology and urinalysis) is conducted pre-treatment and pre-terminal for all dogs. There are pre-study and pre-terminal ECG exams in dogs.

Toxicokinetic sampling (plasma) is done at six timepoints for plasma concentration of test article on first and last day of dosing (samples collected from all animals, analysis performed on samples from all treated animals for all timepoints, plus for control animals at a single timepoint). Plasma samples are analyzed for test material content and the pharmacokinetic parameters ($C_{max}$, $T_{max}$, T, AUC, CL, Vol) are determined. Termination is after 28 days of dosing with complete gross necropsy, organ weights and histopathology on a full tissue list for all animals.

There is an additional group in control and high-dose groups that is similarly dosed for 28 days. After recovery for additional 28 days, the animals are sacrificed with pre-terminal clinical pathology, ophthalmic examination, and ECG. Histopathology on this group of recovery animals is limited to target tissues.

Example 8. Mutagenicity and Genotoxicity Testing (GLP)

Mutagenicity and genotoxicity testing is accomplished by conducting the Ames test, mammalian cell gene mutation assay, and the in vivo mammalian genotoxicity assay. In a promising in silico study performed previously by Leadscope (Columbus, OH), Quantitative Structure Activity Relationships (QSAR) analysis using a battery of predictive models indicated that TXB is predicted to be negative for genotoxic potential.

Ames test. In this assay, TXB is tested for mutagenic activity in *Salmonella typhimurium* strains TA 1535, TA 1537, TA 98 and TA 100 and *E. coli* WP2uvrA at concentrations ranging from 17 to 5,000 micrograms per plate. The highest concentration to be used in this study corresponds to the maximum test concentration recommended in the ICH and OECD guidelines. Two mutation assays (one direct plate and one pre-incubation) are conducted on agar plates in the presence and absence of an Aroclor 1254-induced rat liver preparation and the co-factors required for mixed-function oxidase activity (S9 mix).

Chinese hamster ovary (CHO)/hypoxanthine guanine phosphoribosyl transferase (HGPRT) gene mutation assay. The CHO/HGPRT assay tests for the chemical induction of gene mutations at the HGPRT locus in cultured CHO cells. An initial dose range finding test, with and without metabolic activation, is performed with TXB at 10 dose levels. The definitive test with and without activation is performed at 5 dose levels, with duplicate cultures and a parallel toxicity test. In the study, 6-thioguanine-resistant (6-TG) mutant cells are quantitated following an expression period in culture medium supplemented with 6-TG. Concurrent positive and negative controls are included. n order to evaluate the effect of metabolism on the test article, the tests are performed in the presence and absence of added mammalian liver enzyme preparations (S9). The test is judged negative if there are no statistical increases ($P<0.025$) in the number of 6-TG mutant cells in the TXB incubated cells compared to the vehicle only control.

In vivo genotoxic potential. TXB is evaluated in a micronucleus test in bone marrow erythrocytes of pathogen free ICR (CD-1) mice, 40 males, 40 females (non-pregnant), about 6 weeks old, weighing 20-25 grams, following a 0 hour and 24 hour intravenous dosing and two sampling points at 24 hours and 48 hours after the last dose. This test scores for statistical differences between the frequencies at which micronucleated polychromatic erythrocytes are found in the bone marrow of treated vs. untreated animals. Three concentrations of TXB as well as a positive clastogen and negative (vehicle) controls are administered to groups of mice (5/sex per group). For the TXB treatment group, each animal is administered 2 doses (at the MTD, 0.5 MTD, 0.25 MTD) of TXB, spaced 24 hours apart. The positive clastogen control group is administered daily at 25 mg/kg of cyclophosphamide from day 1 to 4. A vehicle-only control group is included. The animals are observed for signs of toxic and/or pharmacological effects. In the TXB treatment group, a group is sacrificed 24 hours after the last dosing and another group 48 hours after the last dosing. The positive control group and vehicle-only group are sacrificed 24 hours after dosing. The bone marrow of the femora is collected. The bone marrow smears are examined to count approximately 2,000 immature and a corresponding number of mature erythrocytes per animal in each group. Clastogenicity is measured as the proportion of micronucleated erythrocytes.

The test is judged negative if no statistical increases ($P<0.025$) in the numbers of micronucleated polychromatic erythrocytes are observed after dosing animals at the MTD once daily for two days, compared to the control (vehicle only) group.

Example 9. Efficacy of TXB in a Validated Rabbit Model of Tuberculosis (TB)

An acute TB efficacy study is conducted in rabbits, one of the preferred species for TB efficacy testing using IV dosing. For rabbit infection, an aerosol inocula of *M. tuberculosis* strain H37Rv is prepared by diluting frozen pathogen stocks to 106 CFU/ml in phosphate-buffered saline. A total of 20 rabbits are used in the study. The aerosol is generated using a nebulizer delivering filtered air and 6.4 liters/min of aerosol to an inhalation system housed and operated in a dedicated biological safety cabinet. Rabbits having indwelling catheters surgically inserted in the jugular vein for ease of IV drug administration are exposed to the aerosol for 10 minutes, followed by clean air for 5 minutes, and returned to their cages. This procedure delivers approximately 100 CFU/liter of infectious aerosol and generates approximately 50 granulomas per rabbit lung.

The infection is allowed to develop for 9 weeks, after which the rabbits receive daily intravenous doses of TXB for 4 weeks at 10 mg/kg/day and 20 mg/kg/day (as determined from the tolerance and PK study described earlier). The dosing volume of TXB is 2 mL/kg. Oral isoniazid (50 mg/kg/day) is used as a positive control, and is delivered daily by a syringe to the back of the throat. The vehicle control (PPL) is delivered at 20 mg/kg/day, which is the highest concentration of vehicle used in the two TXB dosing solutions. There are 5 animals per study arm. At the end of dosing, a necropsy collects individual lesions and the bacterial burden of the lung, and representative lesions are compared among groups. Endpoints for comparison between groups include lung weights, lymph node weights, lesion volume, histological appearance of lesions, and bacterial burden. The goal is to achieve a ≥1.5 log CFU reduction in lung and representative lesions with no obvious adverse effects in drug-treated animals as compared to vehicle controls.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A pharmaceutical composition, wherein said pharmaceutical composition is an aqueous solution comprising teixobactin (TXB) and a pegylated phospholipid (PPL);

wherein the PPL solubilizes TXB in the aqueous solution; and wherein the PPL is a compound of Formula (I):

(I)

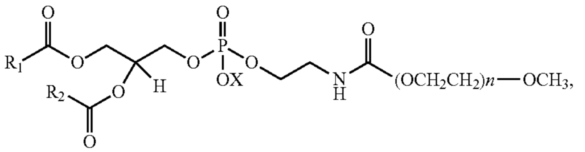

wherein $R_1$ and $R_2$ are independently an alkyl chain comprising from 4 to 50 carbon atoms, from 0 to 10 double bonds or from 0 to 10 triple bonds;

wherein the alkyl chain is unsubstituted or substituted with one or more substituents selected from the group consisting of halogen, —$NO_2$, —COH, —OR', —COR', —OCOR', —COOR', —CONR' and —$SO_4$, wherein R' is hydrogen or a C1-C6 alkyl;

n is an integer from 5 to 1000; and

X is a hydrogen, a monovalent cation or a divalent cation.

2. The pharmaceutical composition of claim 1, wherein $R_1$ and $R_2$ are different.

3. The pharmaceutical composition of claim 1, wherein $R_1$ and $R_2$ are the same.

4. The pharmaceutical composition of claim 1, wherein $R_1$ and/or $R_2$ each comprises from 10 to 20 carbon atoms.

5. The pharmaceutical composition of claim 1, wherein $R_1$ and/or $R_2$ each comprises no double or triple bonds or wherein $R_1$ and/or $R_2$ each comprises at least one double bond.

6. The pharmaceutical composition of claim 1, wherein n is an integer from 30 to 150.

7. The pharmaceutical composition of claim 1, wherein X is selected from the group consisting of hydrogen, $Na^+$, $K^+$, $NH_4^+$, $Ca^{2+}$ and $Mg^{2+}$.

8. The pharmaceutical composition of claim 1, wherein the PPL is a compound selected from the group consisting of:

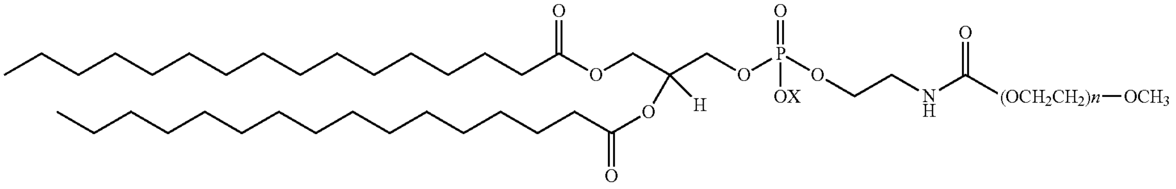

1,2-dipalmitoyl-sn-glycero-3-phosphoethanolamine-N-[methoxy(polyethylene glycol)],

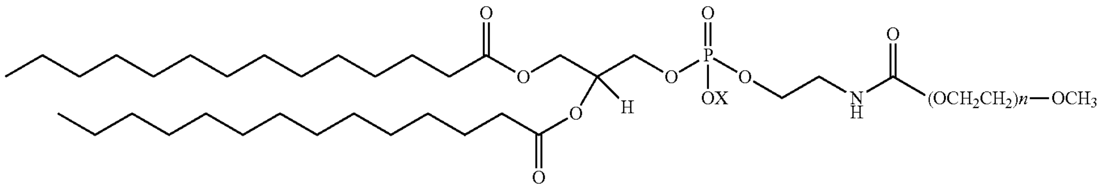

1,2-dimyristoyl-sn-glycero-3-phosphoethanolamine-N-[methoxy(polyethylene glycol)],

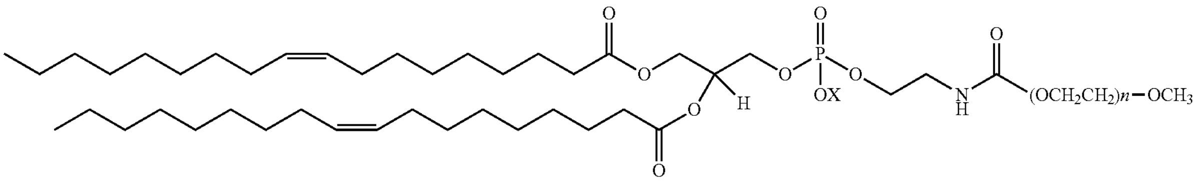

1,2-dioleoyl-sn-glycero-3-phosphoethanolamine-N-[methoxy(polyethylene glycol)], and

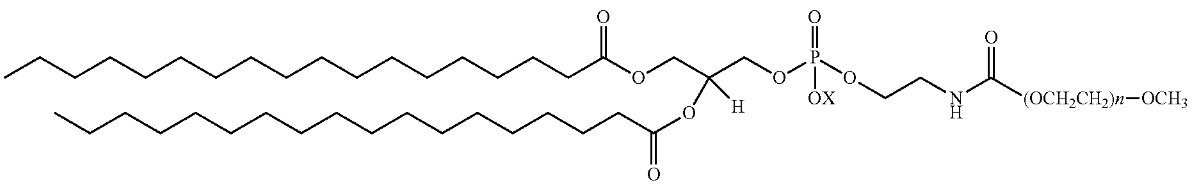

1,2-distearoyl-sn-glycero-3-phosphoethanolamine-N-[methoxy(polyethylene glycol)].

9. The pharmaceutical composition of claim 8, wherein X is $NH_4^+$.

10. The pharmaceutical composition of claim 1, further comprising a carbohydrate.

11. The pharmaceutical composition of claim 10, wherein the carbohydrate is selected from the group consisting of dextrose, glucose, fructose, galactose, lactose, sucrose, ribose, xylose, threose, mannose and mannitol.

12. The pharmaceutical composition of claim 1, wherein the weight ratio of PPL to teixobactin is about 1:1 (w/w) or greater.

13. A method of preparing the pharmaceutical composition of claim 1, comprising the following steps: providing an aqueous solution comprising PPL; and adding teixobactin to the aqueous solution comprising PPL.

14. The method of claim 13, comprising the following steps:

providing an aqueous solution comprising PPL;

adding teixobactin to the aqueous solution comprising PPL; and adding a carbohydrate to the aqueous solution comprising PPL and teixobactin.

* * * * *